United States Patent
Haaije de Boer et al.

(10) Patent No.: US 6,681,768 B2
(45) Date of Patent: Jan. 27, 2004

(54) POWDER FORMULATION DISINTEGRATING SYSTEM AND METHOD FOR DRY POWDER INHALERS

(75) Inventors: Anne Haaije de Boer, Drachten (NL); Henderik Willem Frijlink, Eelde (NL); Doetie Gjaltema, Oosterwolde (NL); Joachim Goede, Hanau (DE); Paul Hagedoorn, Assen (NL)

(73) Assignee: Sofotec GmbH & Co. KG, Frankfurt am Main (DE)

( * ) Notice: Subject to any disclaimer, the term of this patent is extended or adjusted under 35 U.S.C. 154(b) by 47 days.

(21) Appl. No.: 10/177,433

(22) Filed: Jun. 21, 2002

(65) Prior Publication Data
US 2003/0015195 A1 Jan. 23, 2003

Related U.S. Application Data
(60) Provisional application No. 60/300,361, filed on Jun. 22, 2001.

(51) Int. Cl.[7] ........................ A61M 15/00; A61M 16/00; G05D 7/14
(52) U.S. Cl. ........................ 128/203.15; 128/203.12; 604/58
(58) Field of Search ........................ 128/203.12, 203.15; 604/58

(56) References Cited

U.S. PATENT DOCUMENTS

| | | |
|---|---|---|
| 2,587,215 A | 2/1952 | Priestly |
| 3,507,277 A | 4/1970 | Altounyan et al. |

(List continued on next page.)

FOREIGN PATENT DOCUMENTS

| | | |
|---|---|---|
| DE | 24 35 186 | 2/1975 |
| DE | 30 16 127 | 11/1980 |
| DE | 40 04 904 | 9/1990 |
| DE | 39 27 170 | 2/1991 |
| DE | 40 27 390 | 3/1992 |
| DE | 40 27 391 | 3/1992 |
| DE | 42 37 568 | 5/1994 |
| DE | 42 39 402 | 5/1994 |
| DE | 695 19 435 | 9/1995 |
| DE | 696 07 015 | 8/1996 |
| DE | 195 22 416 | 1/1997 |
| EP | 0 069 715 | 1/1983 |
| EP | 0 166 294 | 1/1986 |
| EP | 0 407 028 | 1/1991 |
| EP | 0 424 790 | 5/1991 |

(List continued on next page.)

OTHER PUBLICATIONS

*The tensile strength of powders*, Cheng, Chemical Engineering Science, 1968, vol. 23, pp 1405–1420.
*The Strength of Granules and Agglomerates*, (1962), Rumpf, pp 379–418.

(List continued on next page.)

*Primary Examiner*—Weilun Lo
*Assistant Examiner*—Michael G. Mendoza
(74) *Attorney, Agent, or Firm*—Baker & Daniels

(57) ABSTRACT

A disperser for dry powders which can be used with different dose systems, dose weights ranging from 2 to 25 mg and different types of powder formulation. In one embodiment, the disperser acts both as a de-agglomeration (disintegration; aerosolization) means and as an air classifier for especially adhesive mixtures. Only fine drug particles are emitted whereas the larger agglomerates and carrier crystals are retained by the disperser. Another embodiment enables time controlled release of carrier crystals in these mixtures. Yet another embodiment has optimized performance with spherical pellets, containing no carrier crystals. Other possible embodiments of the invention make it possible to control the total inhaler resistance and the powder deposition in the upper respiratory tract by

U.S. PATENT DOCUMENTS

| | | | |
|---|---|---|---|
| 3,635,219 | A | 1/1972 | Altounyan et al. |
| 3,669,113 | A | 6/1972 | Altounyan et al. |
| 3,906,950 | A | 9/1975 | Cocozza |
| 3,921,637 | A | 11/1975 | Bennie et al. |
| 3,948,264 | A | 4/1976 | Wilke et al. |
| 3,971,377 | A | 7/1976 | Damani |
| 3,991,761 | A | 11/1976 | Cocozza |
| 4,046,146 | A | 9/1977 | Rosskamp et al. |
| 4,147,166 | A | 4/1979 | Hansen |
| 4,338,931 | A | 7/1982 | Cavazza |
| 4,353,365 | A | 10/1982 | Hallworth et al. |
| 4,811,731 | A | 3/1989 | Newell et al. |
| 4,889,144 | A | 12/1989 | Tateno et al. |
| 4,907,538 | A | 3/1990 | Helmle et al. |
| 5,113,855 | A | 5/1992 | Newhouse |
| 5,161,524 | A | 11/1992 | Evans |
| 5,263,475 | A | 11/1993 | Altermatt et al. |
| 5,301,666 | A | 4/1994 | Lerk et al. |
| 5,320,714 | A | 6/1994 | Brendel |
| 5,347,999 | A | 9/1994 | Poss et al. |
| 5,435,301 | A | 7/1995 | Herold et al. |
| 5,437,270 | A | 8/1995 | Braithwaite |
| 5,478,578 | A | 12/1995 | Arnold et al. |
| 5,579,760 | A | 12/1996 | Kohler |
| 5,740,792 | A | 4/1998 | Ashley et al. |
| 5,829,434 | A | 11/1998 | Ambrosio et al. |
| 5,840,279 | A | 11/1998 | Narodylo et al. |
| 5,881,719 | A | 3/1999 | Gottenauer et al. |
| 6,026,808 | A * | 2/2000 | Armer et al. .......... 128/200.23 |
| 6,027,714 | A | 2/2000 | Trofast |
| 6,056,169 | A | 5/2000 | Bruna et al. |
| 6,071,498 | A | 6/2000 | Narodylo et al. |
| 6,138,671 | A | 10/2000 | Noakes et al. |
| 6,232,459 | B1 * | 5/2001 | Lal et al. .................... 536/23.5 |
| 6,257,232 | B1 * | 7/2001 | Andersson et al. .... 128/203.15 |
| 6,347,629 | B1 * | 2/2002 | Braithwaite ............ 128/203.15 |
| 6,367,471 | B1 * | 4/2002 | Genosar et al. ........ 128/200.23 |
| 6,418,926 | B1 * | 7/2002 | Chawla ................. 128/203.12 |

FOREIGN PATENT DOCUMENTS

| | | |
|---|---|---|
| EP | 0 505 321 | 9/1992 |
| EP | 0 547 429 | 6/1993 |
| EP | 0 592 601 | 4/1994 |
| EP | 0 611 577 | 8/1994 |
| EP | 0 776 253 | 6/1997 |
| EP | 0 850 081 | 7/1998 |
| FR | 2 352 556 | 1/1978 |
| FR | 2 447 725 | 8/1980 |
| GB | 1118341 | 7/1968 |
| GB | 1478138 | 6/1977 |
| GB | 2041763 | 9/1980 |
| GB | 2165159 | 4/1986 |
| NL | C1008019 | 12/1998 |
| WO | WO 90/13327 | 11/1990 |
| WO | WO 90/15635 | 12/1990 |
| WO | WO 91/13646 | 9/1991 |
| WO | WO 92/03175 | 3/1992 |
| WO | WO 92/04928 | 4/1992 |
| WO | WO 92/05825 | 4/1992 |
| WO | WO 92/09322 | 6/1992 |
| WO | WO 93/00123 | 1/1993 |
| WO | WO 93/09832 | 5/1993 |
| WO | WO 93/24165 | 12/1993 |
| WO | WO 94/23772 | 10/1994 |
| WO | WO 95/11666 | 5/1995 |
| WO | WO 96/02231 | 2/1996 |
| WO | WO 96/23485 | 8/1996 |
| WO | WO 97/03649 | 2/1997 |
| WO | WO 97/09083 | 3/1997 |
| WO | WO 87/05213 | 9/1997 |
| WO | WO 98/03217 | 1/1998 |
| WO | WO 98/26827 | 6/1998 |
| WO | WO 99/62495 | 12/1999 |
| WO | WO 01/60341 | 8/2001 |

OTHER PUBLICATIONS

European Continuing Education College, Pharmaceutical Aerosols and Dry Powder Systems, Nov. 18–20, 1996, *Powder Technology and Powder Characterization*, Professor Michael Aulton, pp 1–43.

*Dry Powder Aerosols I: A New Powder Inhalation Device*, Bell et al., Journal of Pharmaceutical Sciences, vol. 60, No. 10, Oct. 1971, pp 1559–1564,.

*Inhalation characteristics and their effectrs on in vitro drug delivery from dry powder inhalers*, De Boer et al., International Journal of Pharmaceutics 153, (1997) pp. 67–77.

*Disintegration of weak lactose agglomerates for inhalation applications*, Boerefijn et al., International Journal of Pharmaceutics 172 (1998) pp. 199–209.

*In vitro evaluation of dry powder inhalers I; drug deposition of commonly used devices*, Steckel et al., International Journal of Pharmaceutics 154 (1997) pp. 19–29.

*Effect of surface morphology of carrier lactose on dry powder inhalation property of pranlukast hydrate*, Kawashima et al, International Journal of Pharmaceutics 172 (1998) pp. 179–188.

*The relationship between physical properties of lactose monohydrate and the aerodynamic behavior of adhered drug particles*, Fridrun Podczeck, International Journal of Pharmaceutics 160 (1998) pp. 119–130.

*The role of fine particle lactose on the dispersion and deaggregation of salbutamol sulphate in an air stream in vitro*, Zeng et al., International Journal of Pharmaceutics 176 (1998) pp. 99–110.

*Rupture of dry agglomerates*, Coury et al., Powder Technology 85 (1995) pp. 37–43.

*An investigation into the deposition of inhalation aerosol particles as a function of air flow rate in a modified "Kirk Lung"*, Davies et al., J. Pharm. Pharmac., 28, (1976) pp. 908–911.

Short Communication, *Ordered mixtures—Interactive mixtures*, Egermann et al., Powder Technology, 36 (1983) pp. 117–118.

*Application of Computer Modeling in the Design and Development of the New Mometasone Furoate Dry Powder Inhaler (MF–DPI) Nozzle*, Fan et al., Respiratory Drug Delivery VII, 2000, pp. 491–493.

*Ordered Mixing: A New Concept in Powder Mixing Practice*, J.A. Hersey, Powder Technology, 11 (1975), pp. 41–44

FlowCaps® Information Pack, Hovione 1995.

*Aerosols for inhalation therapy*, W.F. Kirk, Pharmacy International, Jun. 1986, pp. 150–154.

*Dry Powder Inhalation, Technical and Physiological Aspects, Prescribing and Use*, Johannes Petrus de Koning, Thesis, University of Groningen, 2001, ISBN 90–367–1393–5.

*Deposition Patterns of Aerosolized Drugs Within Human Lungs: Effects of Ventilatory Parameters*, Martonen et al., Pharmaceutical Research, vol. 10 No. 6, 1993, pp. 871–878.

*The Effect of Flow Rate on Drug Delivery from the Pulvinal, A High–Resistance Dry Powder Inhaler*, Meakin et al., Journal of Aerosol Medicine, Vol. II, No. 3, 1998, pp. 143–152.

*Flow–dependent effect of formoterol dry–powder inhaled from the Aerolizer®,* Nielsen et al., Eur. Respir. Journal, 1997, vol. 10, pp. 2105–2109.

*Design, Development and Performance of a Multidose Dry Powder Inhaler,* Parry–Billings, et al., Pharmaceutical Technology Europe, Feb. 2000, pp. 38–45.

*"Supersaturated" Ordered Mixtures on the Basis of Sorbitol,* Schmidt, Drugs Made in Germany, Reprint from: Vol, XXVIII, (1985) pp. 49–55.

*Local side–effects during 4–year treatment with inhaled corticosteroids—a comparison between pressurized metered–dose inhalers and Turbuhaler®,* Selroos et al., Allergy 1994, vol. 49, pp. 888–890.

*Easyhaler®, A Novel Multidose Powder Inhaler—Comparison with Metered Dose Inhaler,* Silvasti et al., Drugs of Today, vol. 32, No. 5, 1996, pp. 353–363.

*Order out of chaos,* John Staniforth, J. Pharm. Pharmacol. 1987, vol. 39, 1987, pp. 329–334.

*Added External Resistance Reduces Oropharyngeal Deposition and Increases Lung Deposition of Aerosol Particles in Asthmatics,* Svartengren et al., Am.J. Respir Crit Care Med. vol. 152, 1995, pp. 32–37.

*Drug delivery to the respiratory tract using dry powder inhalers,* Timsina et al., International Journal of Pharmaceutics, 101 (1994), pp 1–13.

*Turbuhaler: A New Powder Inhaler for Administration of Drugs to the Airways,* Kjell Wetterlin, Pharmaceutical Research, vol. 5, No. 8, 1988, pp. 506–508.

\* cited by examiner

CROSS SECTION B-B'

$F_C$ = centrifugal force
$F_D$ = drag force of the air
$(mV)$ = particle momentum Stream lines of the air --→
and
particle trajectories --·--↑

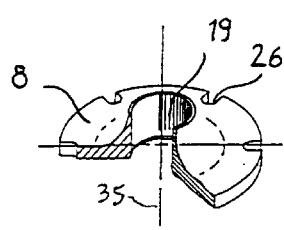
Figure 13B3
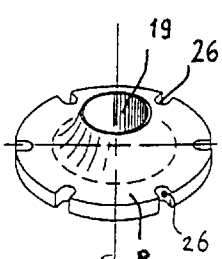
Figure 13B2
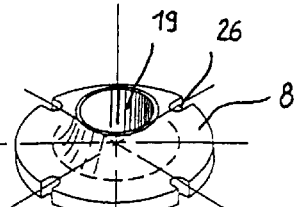
Figure 13B1
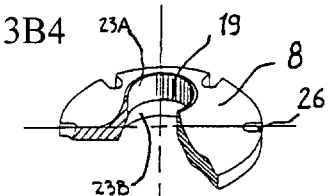
Figure 13B4
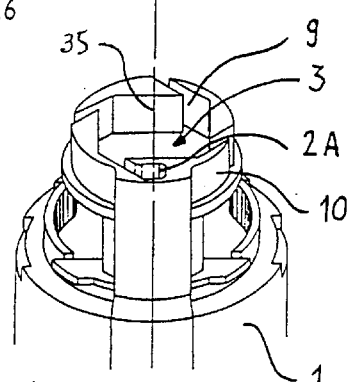
Figure 13A
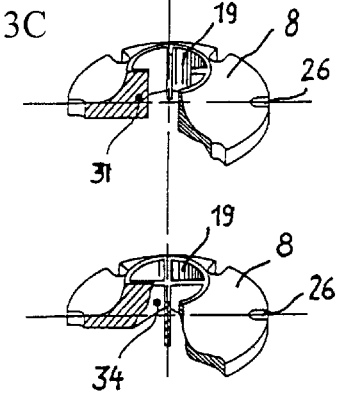
Figure 13C
Figure 13D
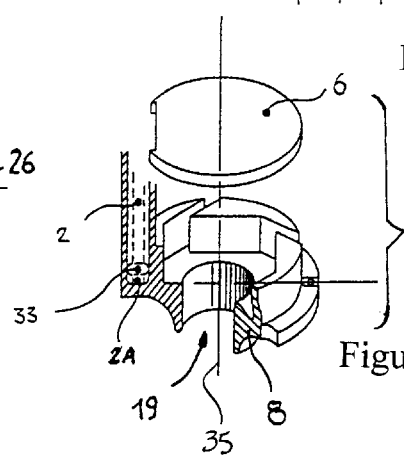
Figure 13E

POWDER FORMULATION DISINTEGRATING SYSTEM AND METHOD FOR DRY POWDER INHALERS

CROSS REFERENCE TO RELATED APPLICATIONS

This application claims priority under 35 U.S.C. 119(e) of U.S. provisional patent application serial No. 60/300,361 filed on Jun. 22, 2001 entitled Powder Formulation Disintegrating System and Method for Dry Powder Inhalers.

BACKGROUND OF THE INVENTION

1. Field of the Invention

The field of the invention is related to dry powder inhalers for delivery of a medicament, or a mixture of medicaments, to the respiratory tract. Dry powder inhalers are designed to store and provide a powder formulation, containing the drug in the correct particle size for effective deep lung deposition, comprising a dosing system for the reproducible administration of the required quantity of powder to the patient, a disintegration system for releasing drug particles from the powder formulation, and a mouthpiece.

2. Description of the Related Art

Dry Powder Inhalers

It is historical tradition to divide dry powder inhalers into (a) single dose, (b) multiple unit dose and (c) multi dose devices. For inhalers of the first type, single doses have been weighed by the manufacturer into small containers, which are mostly hard gelatin capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler. Generally, disassembling of the inhaler is necessary for inserting and removing the capsule, which is an operation that can be difficult and burdensome for some patients. Other drawbacks related to the use of hard gelatin capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported (e.g. Nielsen, K. G., Skov, M., Klug, B., Ifversen, M. and Bisgaard, H. Flow-dependent effect of formoterol dry-powder inhaled from the Aerolizer®, Eur. Resp. J. 10 (1997) 2105–2109).

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e.g., DE 3927170. They comprise the type of multiple unit dose inhalers together with blister inhalers, which have a limited number of unit doses in supply on a disk or on a strip. Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose inhalers do not contain pre-measured quantities of the powder formulation. They consist of a relatively large container and a dose measuring principle that has to be operated by the patient. The container bears multiple doses that are isolated individually from the bulk of powder by volumetric displacement. Various dose measuring principles exist, including rotatable membranes (e.g., EP0069715) or disks (e.g., FR 2447725; EP 0424790; DE 4239402 and U.S. Pat. No. 5,829,434), rotatable cylinders (e.g., EP 0166294; GB 2165159 and WO 92/09322) and rotatable frustums (e.g., U.S. Pat. No. 5,437,270), all having cavities which have to be filled with powder from the container. Other multi dose devices have measuring slides (e.g., U.S. Pat. Nos. 2,587,215; 5,113,855 and 5,840,279) or measuring plungers with a local or circumferential recess to displace a certain volume of powder from the container to a delivery chamber or an air conduit (e.g., EP 0505321, DE 4027391 and WO 92/04928).

Reproducible dose measuring is one of the major concerns for multi dose inhaler devices. The powder formulation has to exhibit good and stable flow properties because filling of the dose measuring cups or cavities is mostly under the influence of the force of gravity. The patient has to handle the inhaler correctly and especially, to keep the device in the correct position while operating the dose measuring principle. Only a few examples are known of special means to facilitate powder filling, e.g., EP 0424790 (vibratory means) and WO 92/04928 (collar-like portion for guiding the powder to the recess in a plunger). For preloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers cannot be agitated by this inspiratory air stream, the powder mass is simply entrained from the cavity and little de-agglomeration is obtained during discharge. Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e.g. U.S. Pat. No. 5,840,279). For such semi-permanent multi dose inhalers with disposable drug containers, the requirements to prevent drug accumulation are even more strict.

Powder Formulations

Many size ranges have been proposed as optimal for inhalation drugs, including 1–5 $\mu$m (WO 95/11666), 0.1–5 $\mu$m (WO 97/03649), 0.5–7 $\mu$m (Davies, P. J., Hanlon, G. W. and Molyneux, A. J. An investigation into the deposition of inhalation aerosol particles as a function of air flow rate in a modified 'Kirk Lung' J. Pharm. Pharmac. 28(1976) 908–911) and 2–7 $\mu$m (Kirk, W. F. Aerosols for inhalation therapy. Pharm. International (1986) 150–154). Particles larger than 7 $\mu$m are deposited mainly in the oropharynx by inertial impaction; most particles between 0.1 and 1 micron are exhaled again as the consequence of their low deposition efficiency in the whole respiratory tract (Martonen, T. B. and Katz, I. M. Deposition patterns of aerosolized drugs within human lungs: effects of ventilatory parameters. Pharm. Res. 10 (1993) 871–878). Different techniques are available for the production of such small particles, e.g., micronization of larger crystals with a jet mill or other comminution equipment, precipitation from (super) saturated solution, spray drying or supercritical fluid methods. Products obtained with different techniques may differ in their surface properties and therefore, in cohesiveness and/or adhesiveness. The degree of particle-to-particle interaction has influence on the de-agglomeration process during inhalation.

The very cohesive nature of micronized particles and the low quantities in which inhalation drugs are administered for obtaining desired therapeutic effects, generally between 10 and 400 µg, with an exception for profylactic (e.g. disodium cromoglycate) and antibiotic (e.g. colistin sulphate) drugs (both in the mg-range), make it very difficult to achieve the necessary reproducibility in the administration to the patient. Therefore, processing of the drug or drug combination into a suitable powder formulation is necessary. Currently, two different types of powder formulation are widely used for inhalers: spherical pellets and adhesive mixtures. Adhesive mixtures are also termed ordered mixtures (Hersey, J. A. Ordered mixing: a new concept in powder mixing practice. Powd. Technol. 11 (1975) 41–44) or interactive mixtures (Egermann, H. Ordered mixtures-Interactive mixtures. Powder Technol. 36 (1983) 117–118). A special type of adhesive mixtures are the nucleus agglomerates, also referred to as supersaturated ordered mixtures (Schmidt, P. C. and Benke, K. "Supersaturated" ordered mixtures on the basis of sorbitol. Drugs made in Germany 28 (1995) 49–55) or core agglomerates (PCT/EP95/02392).

In spherical pellets, the micronized drug particles, with or without micronized (lactose) excipient, have been agglomerated and subsequently spheronized in order to form much larger, spherical and thus, free flowing pellets. The size range of such pellets is approximately between 100 and 2000 µm. No binders have been used, but the amount of water of absorption may have been controlled to increase cohesiveness. Generally, pellets for inhalation are very weak and exhibit very low densities between 0.28 and 0.38 g/cm$^3$ (NL C1008019, 1999).

Adhesive mixtures consist of relatively large crystals, generally alpha lactose monohydrate, carrying the micronized drug particles on their surface. Standard mixing techniques can be used to obtain the desired degree of homogeneity. Good homogeneity and adequate flow properties are not the only prerequisites for good dose reproducibility. However, during inhalation, the drug particles have to be detached from the carrier crystals before they can enter the lower respiratory tract. It has been recognized, that the carrier surface properties play an important role in the drug-to-carrier interaction and thus, on the extent of detachment during inhalation.

There are several reasons why either of the two types of powder formulations can be incompatible with a certain inhaler design. Because of their high sensitivity to impact forces, spherical pellets should preferably not be used in inhalers having a bulk container for the powder in combination with a measuring principle that has to be operated by the patient for the isolation of a single dose. If the inhaler is dropped by the patient, the free flowing pellets may be distorted into a shapeless powder mass that is unable to fill the volumetrical dose measuring cavities in a reproducible way. Adhesive mixtures with low drug concentrations on the other hand, should preferably not be used in combination with preloaded dose compartments having a much larger volume than the powder. Drug particles may be transferred from the carrier crystals to the inner walls of the compartment to an extent of more than 30% of the drug dose. This may result in high losses for the emitted fine particle dose, because the particles that can be transferred easily from the carrier particles to the compartment walls are also the particles of which removal forces during inhalation can get best hold of.

Carrier Materials in Adhesive Mixtures

In adhesive mixtures for inhalation, crystalline alpha lactose monohydrate is most widely used as carrier excipient. The size distribution of the carrier fraction may vary with the specific demands regarding powder flow, drug load, emptying of the dose compartment, fine particle detachment during inhalation and physiological effects from carrier deposition in the respiratory tract, etc. Bell, J. H., Hartley, P. S. and Cox, J. S. G. Dry powder aerosols I: a new powder inhalation device. J. Pharm. Sci. 60 (1971) 1559–1564 found best discharge from pierced hard gelatin capsules in the Fisons Spinhaler for a fraction of 70–100 µm of BP-lactose. Silvasti, M. Sormunen, H., Laurikainen, K., Lähelmä, S. and Toivanen, P. Easyhaler®, a novel multidose powder inhaler—comparison with metered dose inhaler. Drugs of Today 32 (1996) 353–363 described that the lactose size fraction used for the Orion Easyhaler is large enough to avoid deposition of the material in the lower parts of the respiratory tract, without specifying the exact size range. Podczeck, F. The relationship between physical properties of lactose monohydrate and the aerodynamic behaviour of adhered drug particles. Int. J. Pharm. 160 (1998) 119–130 referred more specifically to coarse carrier particles in the size range between 50 and 200 µm, which are physiologically inert. Nearly the same fractions of 30 to 80 µm, respectively 30 to 90 µm are mentioned in U.S. Pat. No. 5,478,578 and by Timsina, M. P., Martin, G. P., Marriott, D., Ganderton, D. and Yianneskis, M. Drug delivery to the respiratory tract using dry powder inhalers. Int. J. Pharm. 101 (1994) 1–13. In WO 95/11666 it is claimed that carrier particles are advantageously between 50 and 1000 µm, preferably less than 355 µm (26 to 250 µm) and even more preferably between 90 and 250 µm to have best flow properties.

The use of granular carrier materials has also been described. Patent application WO 87/05213 describes a 'conglomerate', consisting of a water-soluble vehicle (e.g., lactose) or a mixture of such vehicles and a suitable lubricant (e.g., magnesium stearate) in a size range between 30 and 150 µm as new carrier excipients for inhalation powders. EP 0876814 A1 describes roller-dried beta-lactose in a size fraction of 50 to 250 µm (preferably 100–160 µm) as a suitable excipient for dry powder inhalation. This type of lactose has a granular appearance, and a rugosity between 1.9 and 2.4 is particularly recommended. In the same patent, crystalline α-lactose monohydrate (with a rugosity of 1.75) and spray dried lactose (with a rugosity between 2.4 and 2.8) are rejected as inferior carriers for inhalation drugs.

The effect of carrier surface properties has been studied more in detail by Podczeck and Kawashima, Y. Serigano, T., Hino, T., Yamamoto, H. and Takeuchi, H. Effect of surface morphology of carrier lactose on dry powder inhalation property of pranlukast hydrate. Int. J. Pharm. 172 (1998) 179–188. Podczeck used ten different marketed alpha-lactose monohydrate products for preparing adhesive mixtures with salmeterol xinafoate. The results of the study show that the relationship between the physical properties of the lactose carrier particles and impactor deposition data are complex and that a simple interchange of carrier material by another brand or grade is impossible. It was concluded that crystalline alpha lactose products supplied by DMV International and Borculo Whey Products (both The Netherlands) exhibit a decreasing surface roughness with decreasing particle size, whereas products from Meggle (Germany) show an opposite correlation. Kawashima et al. prepared mixtures of pranlukast hydrate with similar size fractions of completely different types and modifications of lactose and found that the delivered dose from the Spinhaler (at 60 l/min) increases with increasing specific surface area of the carrier fraction, whilst the fine particle dose decreases. They concluded that not the absolute surface roughness of the carrier crystals seems to be important, but rather the scale of the roughness (microscopic versus macroscopic). For granules with so-called 'superparticle' roughness, interparticulate bonds between drug and carrier are high as a result of interlocking. WO 95/11666 describes that the asperities and clefts in the surface of a carrier particle are often found to be an area of high surface energy for which active particles have preference to deposit and are adhered most strongly. Buckton (1997) explains significant differences in physical carrier surface properties by differences in both surface energies and solid-state properties, such as the presence of amorphous material in the carrier crystals.

Treatment of the carrier crystals prior to the mixing with the drug for improvement of their properties as carrier material has been described in WO 95/11666, WO 96/23485 and WO 97/03649. Treatment in WO 95/11666 consists of gently milling of the carrier particles, preferably in a ball mill for several hours at a low rotational speed. During the treatment, asperities such as small grains are dislodged from the carrier surface and attached to the high energy sites in clefts, whereas the size of the carrier particles remains substantially unchanged. WO 96/23485 describes the addition of small amounts of anti-adherent or anti-friction material, such as magnesium stearate, leucine or silicon dioxide, as fine particles to the carrier crystals for the occupation of the active sites.

An increase of the released fine particle fraction from adhesive mixtures during inhalation has also be achieved by adding fine excipient (lactose) particles to these mixtures. Zeng, X. M., Martin, G. P., Tee, S-K. and Marriott, C. The role of fine particle lactose on the dispersion and deaggregation of salbutamol sulphate in an air stream in vitro. Int. J. Pharm. 176 (1998) 99–110 found that the addition of 1.5% of intermediate sized lactose (MMD=15.9 $\mu$m) to an adhesive mixture with salbutamol sulfate and carrier fraction 63–90 $\mu$m increases the fine drug particle fraction from the Rotahaler in the twin impinger (60 l/min) with more than 60%, compared to the mixture without the fine lactose fraction. A further increase to 9% (w/w) of the finer lactose in the blends increased the fine drug particle fraction with another 50%. U.S. Pat. No. 5,478,578 claims that the inhalable portion of the active substance in inhalation powders can be controlled within wide limits, while keeping good accuracy of metering, by combining the micronized active substance with suitable quantities of a mixture of acceptable excipients. One component of the excipient mixtures has to have a mean particle size of less than 10 $\mu$m, whereas the other component has to have a mean diameter of greater than 20 $\mu$m (generally below 150 $\mu$m and preferably below 80 em).

Particle-to-Particle Interaction Forces and Break-up Forces

Adequate powder de-aggregation during inhalation occurs when separating forces exceed the interaction forces between the particles. Separating forces may be generated in different ways and include in currently marketed devices for instance (a) inertial forces on impact of particles against each other or against the inhaler walls, (b) friction or shear forces acting on agglomerates sliding along an inhaler wall, and (c) dispersing forces in turbulent air streams, such as drag and lift forces. In breath actuated dry powder inhalers, separating forces generally become higher with increasing inspiratory effort as the result of increasing air velocity. The effectiveness by which the available energy can be dissipated into rupture or detachment depends on many other factors too, such as the type of formulation (pellets or adhesive mixture) that is subjected to these forces, the order of magnitude for the interparticulate forces in the formulation, and the direction in which the removal forces act on the powder agglomerates, more particularly on drug particles attached to carrier surfaces. Because the particle orientation on impact can not be controlled, repeated collision may be necessary to obtain the correct direction for detachment of such particles.

Previously, it has been described that the surface properties of the lactose carrier crystals may have a dramatic effect on the interaction between drug and carrier particles in adhesive mixtures. They also can have an effect on the removal forces. Drag and lift forces are rather ineffective for the detachment of small drug particles from larger carrier crystals. This is especially the case, when the surface of the carrier crystals is not smooth (as for granulates) and fine particles can be stored away in surface discontinuities. For carrier particles with higher surface rugosities, also friction forces are quite unable to shear off adhering drug particles, simply because these fine particles make no contact with the inhaler walls along which the carrier particles rattle, roll or slide. Inertial forces on the other hand, such as deceleration forces on impact, can be highly effective in the direction of the original particle motion before collision. Fine particle momentum, and thus removal efficiency in this direction, increases not only with increasing air velocity but also with higher mass for the adhering particle, which may also be a small agglomerate of fine particles. Therefore, incomplete break-up of fine drug particles during mixing seems to be an advantage for this type of removal force.

Deceleration forces can only be effective in detaching drug particles, when there is a free path for these particles to move away from the carrier crystal. When the inhaler wall with which the carrier particle collides is obstructing, drug particles in between the carrier and this inhaler wall may become attached even stronger to the carrier surface as before collision. The same is true for particles attached to the opposite carrier surface, or particles obstructed by projections on carrier surfaces perpendicular to the hit inhaler wall, although to less extent, because the increase in attachment force to these carrier surfaces is dependent on the fine particle momentum and not on the much higher carrier momentum. An increase in attachment force is to be expected when the contact area between a drug particle and the carrier crystal can be increased under load. This may, for instance, be the result of the existence of ductile surface layers of lactose impurities. For de-agglomeration principles relying on inertial forces, carrier surface discontinuities may be an advantage, as (a) they are able to provide a free path for detached fine particles and (b) they can store larger fine particle agglomerates that remain intact during the mixing process and have a much higher momentum, being transferred into a removal force on impact, than primary drug entities. Because drug particle detachment from carrier crystals occurs only in one direction and part of the adhering drug particles may become attached even stronger on impact, repeated collision at relatively high velocity is necessary to obtain an acceptable fine particle fraction from adhesive mixtures during inhalation.

The necessary energy for the shattering of soft spherical pellets on impact depends strongly on the structure of these pellets (Coury, J. R. and Aguiar, M. L. Rupture of dry agglomerates. Powder Technol. 85 (1995) 37–45, and Boerefijn, R., Ning, Z. and Ghadiri, M. Disintegration of weak lactose agglomerates for inhalation applications. Int. J. Pharm. 172 (1998) 199–209). Many different theoretical approaches have been presented to predict the strength of granules and compacts, starting with Rumpf, H. in Knepper, W. A. (editor). Agglomeration. Interscience, New York (1962) 379–418 and Cheng, D. C. H. Chem. Eng. Sci 23 (1968) 1405–1420. In most of these approaches, pellet tensile strength is expressed as a function of the mean interaction force per contact point, the size of the primary particles in the pellet and the average coordination number. The assumptions made for these theoretical approaches apply fairly well for micronized inhalation drugs, consisting generally of more or less spherical particles which vary not extremely in size. Moreover, the interaction forces between the particles are all of the same order of magnitude and rupture of the pellets is across the bonding sites between the particles.

Further refinements to the theoretical approaches can be made in terms of interaction force per unit contact area and total contact area between two particles. The coordination number can be expressed in the powder porosity, which is extremely high for soft spherical inhalation pellets. Corresponding with a reported density ($p_P$) of approx. 0.30 to 350.40 g/cm$^3$ (NL C1008019, 1999), porosity values ($\epsilon=1-p_S/p_0$) may be between 0.69 to 0.77 (for a true particle density, $p_0$, of 1.3 g/cm$^3$). Interaction forces between particles in inhalation pellets are generally of the van der Waals type.

Recent work has shown, that defects in pellets may cause the nucleation of cracks along which breakage occurs (Coury and Aguiar, 1995). Such defects reduce the necessary energy for rupture considerably. The extremely porous soft spherical pellets for inhalation exhibit a high degree of discontinuity, representing many defects from which disintegration may start. Boerefijn et al. (1998) showed that the disintegration of soft spherical lactose pellets for inhalation scales with the square of the impact velocity. They also investigated the effect of storage conditions and pellet size on the type and extent of fracture. In contrast with solid materials, they found that smaller pellets have a much higher extent of breakage than larger agglomerates (for pellets stored in a desiccator at 5% relative humidity). They also observed that pellets exposed to 87% relative humidity are far more resistant to breakage than dry pellets, due to a change in interparticulate forces. Fractional losses from dry impacted pellets (between 5 and 30 mass percent) consist primarily of single particles and only a few smaller clusters of primary particles. Samples exposed to 87% RH have much lower fractional losses on impact (between zero and twelve mass percent) which consist of small flakes well below the original pellet size. The nuclei of dry pellets were found to deform much stronger as the result of internal shear than wet agglomerates, exhibiting rather a semi-brittle failure mode.

Analogous to adhesive mixtures, different types of separation forces are quite different in their efficiencies to break up soft spherical pellets. Drag forces (e.g., in turbulent flow regions) are not so effective when pellets are already airborne. But when the pellets are forced into a dose compartment and an air flow is suddenly conducted through this compartment at high velocity, the powder may be disrupted to large extend and be lifted from the compartment rather as smaller fragments than in bulk. Drag forces are particularly effective in disrupting such a powder when the air flow can pass through the highly porous powder mass itself instead of through large interparticular pores; i.e., when the pellets have been united into one powder lump. For this principle, a very high flow increase rate towards peak flow rate is necessary. But it can also be achieved by sudden expansion of the air inside a powder mass, e.g., by creating an under-or overpressure in the pore volume of the powder in a closed dose compartment relative to the pressure in an adjacent spacer first, and next connecting the dose compartment quite abruptly with the much large spacer volume.

Friction forces are highly effective for de-agglomeration of soft spherical pellets, as has been shown for the Astra Turbuhaler (e.g., Steckel, H. and Müller, B. W. In vitro evaluation of dry powder inhalers I: drug deposition of commonly used devices. Int. J. Pharm. 154 (1997) 19–29; De Boer, A. H. Bolhuis, G. K., Gjaltema, D. and Hagedoorn, P. Inhalation characteristics and their effects on in vitro drug delivery from dry powder inhalers. Part 3: the effect of flow increase rate (FIR) on the in vitro drug release from the Pulmicort 200 Turbuhaler. Int. J. Pharm. 153 (1997) 67–77 and De Koning, J. P. Dry powder inhalation; technical and physiological aspects, prescribing and use. Thesis, University of Groningen, 2001. ISBN 90-367-1393-5). The majority of the dose in pellets can be fractured into much smaller entities during a relatively short passage through an air duct with a helical insert, yielding in vitro fine particle fractions between 40 and 60% of the label claim. During contact between the pellet and the inhaler walls, friction forces, and also van der Waals attraction forces, are directly and solely imposed on the primary particles along the periphery of the pellet which separate them from the mother pellet as primary entities or as small clusters. A disadvantage of this principle is that the van der Waals forces, and possibly also Coulombic forces, cause these smaller entities to adhere to the inhaler wall to quite large extent. Inhaler accumulations of 15 to 25% of the dose are quite usual.

Most effective for spherical pellets are also inertial forces however. Because of their highly porous and rather anisotropic structure, pellets can be deformed quite easily on impact. This deformation causes internal shear and disruption, resulting in the separation of fragments, as observed by Boerefijn et al. (1998). When the pellets are circulating with high velocity in an aerosilization chamber for a certain duration of time, repeated collision between particles and the chamber wall or collision of particles between each other can be realized, so as to complete disintegration of larger separated fragments.

Because different types of separation forces may have different efficiencies for the same type of formulation, unfavorable combinations exist for the powder formulation and the de-agglomeration principle. As discussed previously, drag and shear forces in turbulent air streams are very ineffective with respect to fine drug particle detachment from carrier crystals in adhesive mixtures. Incomplete disintegration for this type of formulation may also be achieved in air conduits with helical inserts. For spherical pellets on the other hand, good de-agglomeration can be obtained in such air channels, as well as in circulation chambers in which repeated collision between particles or particles and the inhaler wall occur. But the intensive particle-to-wall contact must not result in substantial losses of the dose by particle adhesion onto this wall. Optimization in respect of (a) degree of pellet fracture and (b) fine particle accumulation is necessary.

The incompatibilities have the implication, that powder formulations can not be exchanged at will for a given type of de-agglomeration principle, since inadequate disintegration or severe losses of drug particles from adhesion may be the result. This reduces the versatility of an inhaler concept considerably.

Powder De-Agglomeration in Dry Powder Inhalers

In many breath controlled dry powder inhalers, powder de-agglomeration is connected with the emptying of the dose system. The whole, or part of the inspiratory, respectively an auxiliary air flow is directed into, through or past the dose compartment in which a single dose has been weighed, in order to empty the compartment and to transport the dispersed powder to the respiratory tract, as described for example in GB 1118341, DE 3016127, U.S. Pat. Nos. 4,811,731, 5,113,855, 5,840,279 and WO 92/09322.

The air flow may be turbulent or exhibit special flow patterns to disperse the powder by means of shear and drag forces or by particle-to-particle collisions (e.g., Hovione, FlowCaps Information Pack, Ref. no. DY002-rev.4 (1995)), or the air flow may cause the dose container to start a certain (spinning or vibrating) motion by which dose discharge and de-aggregation is promoted. These are particularly mechanisms used for capsule inhalers, as described for example in U.S. Pat. Nos. 3,507,277; 3,669,113; 3,635,219; 3,991,761; FR 2352556; U.S. Pat. Nos. 4,353,365 and 4,889,144. A major disadvantage of capsule inhalers is that the spinning, oscillating or vibrating motion of the capsules during inhalation causes intensive contact between the powder and the inner capsule walls, and the friction and shear of powder along these walls often results in substantial drug accumulation. In contrast with capsules, blisters can not easily be subjected to vibratory or spinning motion.

It has been recognized that simply conducting (part of) the inspiratory air stream through or past the dose compartment does not yield the desired degree of break-up for the powder agglomerates. Different solutions for improvement of the powder dispersion have been proposed, varying from the introduction of (a) narrow air passages, such as venturi tubes, in order to increase local air velocities, (b) impact baffles, plates or walls, positioned in such a way in the air stream that large, inert agglomerates impact against them, (c) air channels in which the air is forced to take a tortuous path, e.g., by means of helical inserts, and (d) special circulation chambers in which particles circulate and impact against each other or against the chamber walls.

Examples of narrow air passages for the particle laden air stream have been disclosed in U.S. Pat. No. 2,587,215, FR 2447725, DE 4027391 and WO 93/09832. More specifically, narrow channels of the venturi type are known from, e.g., U.S. Pat. No. 4,046,146, GB 2165159, U.S. Pat. No. 5,161,524 and 5,437,270. De-agglomeration means of this type may exhibit rather high air flow resistances and the total surface area of the inhaler walls making contact with the micronized drug particles is quite large, which is a disadvantage from the viewpoint of fine particle adhesion onto these walls. Moreover, local high air velocities in a venturi throat, may facilitate powder entrainment from the dose cavity in this region by suction (Bernouilli-effect), but the high velocity is unlikely to result in extreme turbulences that facilitate powder disintegration, because venturi tubes are basically designed to minimize turbulent flow.

Inhalers utilizing impact walls or baffles also include devices with bent mouthpiece sections. The obstructions in the air conduit cause the particle laden air flow to change its direction. Larger particles with much higher inertia than the air, are unable to follow the tortuous path and impact against the obstructions, which is supposed to result in shattering of the agglomerates. The use of baffles in an extension to the inhaler is described in WO 92/05825, whereas de-agglomeration by particle impaction on the inner surfaces of the mouthpiece is for instance claimed by Parry-Billings, M., Boyes, R. N., Clisby, L. M., Braithwaite, P., Williamson, S. and Harper, A. E. Design, development and performance of a multidose dry powder inhaler. Pharm. Technol. Europe (February 2000) 38–45 for the Clickhaler multi dose inhaler.

Inhaler devices, in which the inspiratory air stream with particle agglomerates is conducted through mouthpiece channels with insert bodies or special inner profiles, are numerous. Often, the insert bodies have a helical shape, forcing the air stream to follow a spiral path. Particles in the air stream are subjected to a centrifugal force and tend to concentrate on the outside of the helical passageway. In this outer peripheral region, the more or less spherical pellet type of agglomerates roll along the cylindrical wall of the discharge channel. The friction and shear forces involved, cause primary particles or small clusters to be separated from the outer shell of the pellets. The much more irregular carrier particles in adhesive mixtures rattle, rather than roll, along the channel wall and the repeated collisions may lead to detachment of adhering drug particles. Examples of mouthpiece channels with helical insert bodies are given in, e.g., U.S. Pat. No. 4,907,538, 40 EP 0424790 and EP 0592601. An inhaler with a so-called fluted chimney, having a hexagonal cross section, is described in U.S. Pat. No. 5,829,434. Particles, entering the chimney in a spiral path motion, collide repeatedly with the inner walls of the chimney, thus transfer their kinetic energy into fine particle detachment or agglomerate break-up.

De-agglomeration principles consisting of special circulation chambers, in which particles circulate and impact against each other or against the chamber walls will be described more in detail hereafter.

The degree of powder de-agglomeration in breath controlled dry powder inhalers by all previously mentioned disintegration principles, is determined by the patient's inspiratory effort, i.e., inhaler performance is dependent on the inhalation manoeuvre. If the effort does not meet the requirements for a particular inhaler design, entrainment and fine particle generation may be incomplete. Consequently, drug deposition in the target area may be insufficient for obtaining the desired therapeutic effect. Even with maximal effort, the peak pressure drop across a dry powder inhaler is limited to approximately 2 to 20 kPa, whereas the maximal total volume to be inhaled is between 1 and 3 liters, both depending on the patient's clinical picture and age, and more particularly the inhaler resistance to airflow.

It has been recognized that it is practically impossible to design a de-agglomeration principle which gives a consistent degree of powder de-agglomeration over a wide range of flow rates, when this principle derives its energy solely from the inspiratory air stream (WO 94/23772). The underlying reason for this, is that higher inspiratory air flow rates tend to lead to higher air velocities inside the inhaler and thus, higher impact or shear forces and higher turbulences. At higher effort, simply more energy is available for breaking up the particle agglomerates.

Several approaches have been presented to reduce or eliminate the variability in the fine particle output of breath controlled dry powder inhalers as the result of a variation in inspiratory flow curves. For instance, the application of valves has been proposed, opening first after a threshold flow rate for good disintegration has been achieved by the patient (e.g., U.S. Pat. No. 5,301,666). U.S. Pat. No. 5,161,524 discloses a maximum velocity regulator, positioned within a secondary air flow channel. More complex solutions are disclosed in WO 94/23772 for an inhaler having a compensating de-agglomerate geometry for changes in air flow, and DE 4237568 for the generation of an underpressure in a dispersion chamber.

Inspiratory effort depending dose discharge and powder de-agglomeration can also be eliminated by utilizing pressurized air or mechanically generated underpressures. Moreover, much higher pressure differences across the powder dispersion system can be applied (>100 kPa, equals 1 bar, for overpressures). The aerosol can be discharged from the dose system into a spacer chamber before it is inhaled, and inhalation can be at relatively low flow rates, thus to reduce throat deposition. An average flow rate (Φ) of 30 L/min is quite reasonable for a breath controlled inhaler with a moderate air flow resistance (R) of 0.04 $kPa^{0-5}.min.L^{-1}$. From this, an average pressure drop (dP) during inhalation of 1.44 kPa ($1.44\times10^3 N.m^{-2}$) can be calculated, using the simplified equation for an orifice type of flow constriction: $\sqrt{dP}=R.\Phi$. Also reasonable for this inhaler resistance, is a total inhaled volume (V) of 1.5 Liters ($1.5\times10^{-3}$ $m^3$), corresponding with a total energy (E=V.dP) of 2.16 Nm being available for powder dispersion. Spacer chambers have relatively small volumes to keep the dimensions of the inhaler within acceptable limits. But even for a spacer with a volume of only 250 ml, an average pressure drop of not more than 8.64 kPa (≈0.09 bar) would be necessary to generate the same energy and thus, the same degree of powder break-up by the same disintegration principle. Designs and efficiencies (in utilizing the available energy) of disintegration principles may be different, however. Examples of dry powder inhalers that apply pressurized air systems for powder de-agglomeration are disclosed in DE 2435186, U.S. Pat. Nos. 3,906,950, 5,113,855, DE 4027391 and WO 9962495.

Other ways of applying auxiliary energy for discharge of the dose compartment and powder de-agglomeration is (a) by means of electrically driven impellers, as described in e.g., U.S. Pat. Nos. 3,948,264, 3,971,377, 4,147,166 and WO 98/03217 or (b) with a battery powered piston, tapping drug particles from a tape (WO 90/13327). Systems with auxiliary energy are often voluminous and sensitive to substantial fine drug particle adhesion onto their large inner walls, or have a complex design and structure and are vulnerable in respect of battery failure.

A special group of dry powder inhalers which are more or less independent of the patient's inspiratory effort in respect of dose emission accuracy and fine particle output is constituted by the scraper systems. EP 0407028, DE 4027390 and W093/24165 describe cutting, scraping or eroding principles that remove small quantities of powder from a drug compact by rotational movement of the abrasive blades against the compact over a predetermined angle of rotation. EP 0407028 describes the combination of such a principle with a cyclone chamber, in order to select only the finer particles for inhalation and to spread out more evenly the bolus of the entrained powder, so that the dose of medicament is inhaled over a longer period of time. The scraper principles share the problem of tabulating of the micronized powder, which has to yield a completely isotropic compact, maintaining a constant hardness under different ambient conditions. It is rather problematic to obtain the desired drug size distribution for inhalation by scraping off parts of such a compact.

Prior Art

Most of the previously described de-agglomeration principles have one great disadvantage in common: the discharge of the dose from the inhalation device occurs rather momentarily. The residence time of the powder in the de-agglomeration means is extremely short, relative to the total period during which air is drawn through the inhaler device. Therefore, the efficiency in utilizing the available energy is quite low and most of the air is used only for transport of the generated drug particles into the respiratory tract. As a result, de-agglomeration of the powder, especially that of adhesive mixtures, is often very incomplete and the amount of released drug particles in the desired size range is quite low (20% to 40% of the nominal dose). In accordance with that, an optimal therapeutic effect from a dose is not obtained. In addition, all particles are discharged from the inhaler, without regard to their size. For some drugs, this may be undesirable because of serious adverse side effects from deposition in the mouth and throat. For example, it has been reported that cortico steroids initiate hoarseness and Candidiasis after deposition in the throat (Selroos, O., Backman, R., Forsén, K-O., Lö froos, A-B., Niemistö, M., Pietinalho A., Äkäs C. and Riska, H. Local side-effects during 4-year treatment with inhaled corticosteroids—a comparison between pressurized metered-dose inhalers and Turbuhaler®. Allergy 39 (1994) 888–890).

De-agglomeration principles consisting of special circulation chambers, from which particles can be discharged more gradually into the respiratory tract, may reduce these disadvantages. Generally, circular flow patterns inside such chambers are created by the construction of one or more tangential inlet channels that end at the cylindrical wall of the disk-shaped (or tube-shaped) chamber. The residence time of the powder inside the chamber may be influenced by balancing the drag force and centrifugal force, and in the extreme situation where the centrifugal force is dominant, the tangential flow provides the possibility to retain larger particles by centrifugal separation. The invention disclosed in this patent application is of the circulation chamber type of de-agglomeration principle. It is a modular concept with different modifications, each of these modifications having quite distinct features. Previously disclosed de-agglomeration principles that are particularly relevant to this invention are either those of the same type (circulation chamber), or those being of a different type but sharing one or more of the same features, including (a) residence time control, (b) large particle detainment and (c) control of air flow resistance, as will be explained more in detail hereafter.

Inhalers with internal circulation chambers, have been described in, e.g., GB 1478138, FR 2447725, DE 4004904, EP 0407028, WO 91/13646, WO 92/04928, EP 0547429, DE 4239402, DE 19522416 and PCT/NL01/00133. A very early concept of a tangential flow chamber is disclosed in GB 1118341. This patent describes an open cup (e.g. capsule) for the powder dose which is placed on an upright support rod in the center of a hollow chamber. An air jet, entering through a hole in the lid on the chamber, is directed into the cup to discharge the powder. Supplementary air streams, entering through radial inlet holes in the cylindrical wall of the chamber at the same level as the open end of the powder cup, are forced into a tangential pathway by special air barriers or swirl reversals. The turbulence in the circular air stream is expected to assist in the dispersion of the powder in the air stream.

A basically similar concept is disclosed in GB 1478138. The inhaler consists of a cylindrical container with a mouthpiece tube, having the same longitudinal axis, but a smaller diameter than the container. The connection between both parts is through a narrow tubular extension of the mouthpiece tube, protruding into the container. Also the outlet of the mouthpiece is through a narrow tube, protruding into the mouthpiece cylinder. Air enters the device through two sets of vents, creating a vortex motion inside the container as well as in the mouthpiece cylinder. The powder, being placed inside the container, is entrained in the circulating air stream. The centrifugal force causes the heavier particles to fling outwards against the walls of the container, whereas the finer particles will be drawn through the narrow tubes into the respiratory tract by the action of the drag force.

A completely different design for a circulation chamber is disclosed in DE 4004904 A1. A discharge channel splits the particle laden air flow into a main stream and a side stream; the latter entering a cyclone-like (disk-shaped) circulation chamber. In the region where the air flow is split up, the main stream is directed upwards by a 90 degrees bend in the air conduit, when the inhaler is held in the correct position during inhalation. In the vertically directed passageway downstream of the bend, the drag force is opposite to the force of gravity. This causes larger agglomerates to fall down on the bottom of the channel, whereas only fine particles can be dragged further towards the mouthpiece of the inhaler. The settling agglomerates assemble at the site where the side stream returns to the main stream after a 180 degrees rotation in the cylindrical chamber has been made. The turbulences in this region disintegrate the agglomerates until they have become small enough to be transported by the drag force of the main stream towards the inhalers mouthpiece.

The circulation chamber described in EP 0407028 A2 is referred to as a particular arrangement of air passageways or cyclone means, within which entrained drug particles may circulate. The particle laden air enters the chamber through a single air inlet which is tangential to its cylindrical wall. A venturi adjacent to the junction of the inlet channel with the cyclone chamber accelerates the air flow into this chamber. Discharge of the chamber is through an outlet channel along the longitudinal axis of the chamber. The claimed advantages of the arrangement are that (a) only the finer particles in a particle population of various sizes are selected for inhalation, whereas (b) the bolus of the entrained powder is spread out more evenly, so that the dose of medicament is inhaled over a longer period of time. The cyclone chamber is described in combination with a consolidated medicament supply and a scraping blade as dose measuring means. Comparable circulation or vortex chambers of different designs with one tangential inlet channel are presented in WO 90/15635. The concepts differ in the position of the outlet channel and in the diameter and shape of the vortex chamber, being either a tube, a disk, or a disk with a funnel shaped section towards the outlet channel, having the same longitudinal axis as the vortex chamber.

A disk-shaped cavity with two opposing specially shaped inlet channels providing a turbulent air stream inside the cavity, is mentioned in FR 2447725. In the patent, it is described that de-aggregation does not take place in the cavity, but rather in a helical insert region inside the central suction tube of the inhaler, being also the outlet channel of the cavity. For the marketed concept of this invention, the Pulvonal high resistance dry powder inhaler described by Meakin, B. J., Ganderton, D., Panza, I. and Ventura, P. The effect of flow rate on drug delivery from Pulvinal, a high-resistance dry powder inhaler. J. Aerosol Med. 11 (1998) 143–152, the cavity is referred to as an aerosolization chamber. It is now claimed that de-agglomeration takes place in a narrow passage between the centrally elevated bottom of this aerosolization chamber and the suction tube above that.

WO 92/04928 refers to a so-called wirl mixing chamber which has the shape of a disk with a rounded cylindrical wall. Suction takes place through tangential air channels entering the chamber through holes in its rounded wall. Inside the whirl mixing chamber, a first air flow is guided along the powder compartment and a second air flow collides with the first air flow in substantially traverse direction. This is to mix the air and the powder in a desired manner. In another example, the powder is discharged into the camber from an off center extruder-like dosing mechanism.

EP 0547429 A1, DE 19522416 A1 and PCT/NL01/00133 disclose different concepts, each for a different application, of basically the same type of circulation chamber. In the basic principle described in EP 0547429 A1, the powder laden air flow from the dose compartment is mixed with a particle-free air flow before the mixture of both flows enters a cyclone chamber through specially shaped slits in a central tube protruding from the cyclone bottom into the chamber. The slits create a tangential flow pattern inside this chamber, which has a cylindrical shape with truncated cones at the top and bottom of the cylinder. The mixing of the partial air flows is to increase the particle velocity inside the cyclone chamber, thereby increasing the de-agglomeration forces, particularly those for adhesive mixtures. Discharge of detached fine drug particles is through a special channel that is co-axial with the cylindrical axis of the cyclone chamber and partly projecting into this chamber. The discharge channel widens towards the patient's mouth to reduce particle velocity at entrance into the respiratory tract and to prevent sustained cyclone action inside this channel. Another part of the inspiratory air flow is used to create a particle-free co-axial sheath flow around the aerosol cloud of fine drug particles. The central inlet conduit for the inspiratory air can have a special valve, opening first after sufficient pressure drop is generated by the patient to guarantee good dose entrainment and powder de-agglomeration. In an alternative design, the circulation chamber has a rounded bottom, whereas the tangential air streams are from the cylindrical wall of the chamber.

PCT/NL01/00133 describes an application of this basic type of de-agglomeration principle for a colistin sulfate formulation. Because the high powder load from the high colistin dose in CF therapy can be a burden for the patient, the concept has been modified especially to retain larger excipient crystals in the formulation by inertial separation. Consequently, powder deposition in the respiratory tract can be confined to the active ingredient only. The excipient particles in the formulation for this type of de-agglomeration principle do not act as carrier or as diluent, but as a sweeper, removing adhering fines of the active substance from the internal surface of the disintegration chamber. The formulation may be a physical mixture in which there is no noticeable interaction between the sweeper crystals and the drug particles, as in adhesive mixtures. This has the advantage that the carrier surface properties are irrelevant to the fine particle fraction obtained during inhalation.

The specific design disclosed in PCT/NL01/00133 is not applicable for the spherical pellet type of formulation without sweeper crystals, because of the severe fine particle adhesion onto the inner walls of the circulation chamber. For this application, a third concept has been developed, as described in DE 19522416 A1. The concept has the same cylindrical chamber as the basic concept in EP 0547429 A1, but the mixing of particle laden flow (powder flow) with a particle-free air flow is now inside the chamber instead of in the air channel towards this chamber. In the example shown, the number of so-called bypass channels for the additional air flow is seven, but there may be more, as well as fewer channels. In addition, there is a tangential eighth slit for the powder flow. Discharge from the de-agglomeration chamber is through a channel starting at the centre of the cylindrical end of the disk-shaped chamber, having the same longitudinal axis as this chamber. In the modification described in DE 19522416, the discharge channel does not project into the de-agglomeration chamber. This discharge channel has a minimal length and a strongly reduced diameter to minimize fine particle losses by adhesion onto its inner walls. The concept in DE 19522416 can also be used for adhesive mixtures, although the de-agglomeration efficiency is somewhat lower than that for the concept disclosed in PCT/NL01/00133.

In contrast with the concept in PCT/NL01/00133, there is no large particle retainment. Large particles are discharged from the de-agglomeration chamber gradually with a rate being predetermined by dimensions of the chamber and the carrier size distribution. A certain residence time inside the de-agglomeration principle is considered as an advantage, as has been discussed previously and will be explained more in detail hereafter. The time required for total discharge should not exceed the total inhalation time however. Recent guidelines prescribe that the total drug dose is inhaled within 2 Liters, which corresponds with an inhalation time of 2 seconds at an average flow rate of 60 l/min.

The type of de-agglomeration principle described in EP 0547429 A1, DE 19522416 A1 and PCT/NL01/00133, has a particle-free sheath flow that can reduce the deposition of fine particles in the patient's mouth from return flows. The sheath flow is particularly effective for spherical pellets, because the emitted aerosol cloud generated from this type of formulation does not contain large agglomerates with high inertia that can migrate through the thin sheath of clean air under the influence of the centrifugal forces in the spiral path discharge flow pattern. For adhesive mixtures, the importance of the sheath flow is mainly confined to keeping the inhaler's air flow resistance within acceptable limits.

DE 4239402 A1 describes a complex combination of a residence chamber with a delivery chamber and a disintegration chamber for inhalation powders that may either consist of spherical pellets or be an adhesive mixture. The residence chamber is a disk-shaped part of the air passageway between the dose measuring system and the outlet of the mouthpiece. Its longitudinal axis is perpendicular to the longitudinal axis of the mouthpiece cylinder. The particle laden air passes through an acceleration channel, ending along the periphery of the residence chamber, and is discharged tangentially into this chamber. The air outlet channel of the residence chamber is at a cylindrical end, coaxial with the cylindrical axis of the residence chamber. It ends in an adjacent delivery chamber that is also disk-shaped and has the same longitudinal axis as the residence chamber. Connected to the delivery chamber is a tangential outlet channel, referred to as disintegration chamber. The acceleration channel towards the residence chamber, the outlet channel of the delivery chamber and the mouthpiece cylinder have parallel longitudinal axes. It is claimed that discharge of the powder from the residence chamber is rather gradual and that the majority of the dose is not yet released before peak flow rate has been achieved by the patient. As for the previously described principle, the sustained residence maximizes utilization of the dispersion forces. Further de-agglomeration takes place in the disintegration chamber into which the powder flow is accelerated from the intermediate delivery chamber. At the patient's end, the disintegration channel widens in order to slow down air and particle velocity. This reduces mouth and throat deposition.

All previously mentioned circulation chambers are integral to a particular inhaler design. In contrast, WO 98/26827 refers to a powder de-agglomeration and particle classifying principle that is in fact an extension of the mouthpiece of a dry powder inhaler. The patent application refers to earlier dry powder inhaler developments in which cyclone chambers have been used for (a) the purpose of effecting de-agglomeration and/or (b) separating from each other the heavier and lighter particles in an air/powder mixture. Such a use of cyclones is rejected by the authors, because the efficiency in either of the mentioned applications is determined by the power of suction that a patient is capable of applying to the mouthpiece. For the invention disclosed in WO 98/26827, the primary function of a cyclone chamber is neither to effect de-agglomeration nor to separate particles upon size, but to retain in orbit the heavier particles that have previously been separated from the lighter particles by a 'circulatory section' upstream of the cyclone chamber. In a given example, this circulatory section is a frusto-conical body fitting closely in a funnel-shaped housing. The flow duct is in the form of one or more passageways of helical conformation along the tapered circumference of the frusto-conical body, between this body and the funnel-shaped housing. The conversion from axial towards helical flow is quite abrupt against the top of the frusto-conical body. Particles are being de-agglomerated upon impaction against this surface. It is claimed that the finer and larger particles separate to large extent in the helical passageways by centrifugal action, the finer particles following a spiral path with smaller radius than the larger particles.

Downstream of the circulatory section of this invention, the air is conducted from the passageways near the inner wall of the funnel-shaped housing towards the central axis of this housing along the bottom of the frustum. In this flow region, where the drag force is opposite to the centrifugal force, further classification takes place. Only fine particles are next discharged through the outlet conduit which is co-axial with the axis of the frustum through a narrow passage in a lid on the funnel-shaped housing. Large particles continue to circulate during inhalation in a cyclone chamber adjacent to the circulatory section, or accumulate at the base of this chamber, but detached fine particles during this circulation are not discharged into the respiratory tract because there is no flow from this chamber to the tract.

Another special application of a circulation chamber is presented for the Asmanex (Mometasone Furoate) Twisthaler (U.S. Pat. Nos. 5,740,792, 5,829,434, and Fan, B. J., Yang, T. T. and Kenyon, D. Application of computer modeling in the design and development of the new mometasone furoate dry powder inhaler (MF-dpi) nozzle. Resp. Drug Delivery VII (2000) 585–587.). The nozzle of the Twisthaler for breaking up powder agglomerates includes (a) cavity means, (b) swirl means and (c) chimney means. Cavity means and swirl means constitute a so-called swirl chamber (Fan et al., 2000). Particles entrained from the dose metering cavity by (part of) the inspiratory air, travel through the inhalation channel towards the swirl chamber. This swirl chamber is basically a cylindrical hollow chamber with an internal wall (swirl means) traversing this chamber in an arcuate path. The wall is meant to deflect the particle laden air stream into a tangential pathway. The imparted swirl remains when the air passes through the chimney. As a result, the powder agglomerates that are carried by the air, having a much higher inertia than the air, constantly impact against the inner walls of the swirl chamber and the air conducting swirl wall traversing this chamber (U.S. Pat. No. 5,829,434). Agglomerates also collide with each other, which results in a mutual grinding or shattering action between them. It is described that the particles accelerate to a critical velocity for disruption inside the swirl chamber by the addition of secondary airflow in this chamber (Fan et al., 2000 and U.S. Pat. No. 5,829,434). In contrast with the patent (U.S. Pat. No. 5,829,434), Fan et al. explain that the powder-to-wall collisions in the chimney is the key break-up mechanism in the formation of fine particles for inhalation. For a better effectuation of this fine particle break up in the chimney, the inner walls of this part of the de-agglomeration means have been provided with fluted edges (e.g. to yield a hexagonal cross section).

Some of the previously described concepts have specific drawbacks or limited applications. One of the possible consequences of the application of a circulation chamber is the increase in total air flow resistance of the inhaler, as for instance described by Meakin et al. (1998) for the Pulvonal dry powder inhaler. Especially for concepts having more than one chamber, as described in DE 4239402, the increase must be substantial. Although a high resistance is not unconditionally a disadvantage (e.g., Svartengren, K., Lindestad, P.-A., Svartengren, M., Philipson, K. Bylin, G. and Camner, P. Added external resistance reduces oropharyngeal deposition and increases lung deposition of aerosol particles in asthmatics. Am. J. Respir. Crit. Care Med. 152 (1995) 32–37), patients with reduced pulmonary power must be able to generate sufficient air flow for adequate performance of the device. This is required irrespective of the design of the de-agglomeration principle, unless a constant external energy source for dose entrainment and powder de-agglomeration is used. The pre-separation of particles in a circulary section of the flow duct upstream of the cyclone chamber, as disclosed in WO 98/26827, does not reduce or eliminate this problem, because the detachment of the fine particles from the carrier crystals still depends on the size of the separation forces in this section.

A major concern is the fine particle adhesion onto the inner walls of circulation types of de-agglomeration means, as described in PCT/NL01/00133. The total surface area of inhaler parts making contact with fine drug particles is often quite large, as for DE 4239402, WO 98/26827 and U.S. Pat. No. 5,829,434. At regular time intervals, the de-agglomeration means of this type must be disassembled for inspection and/or cleaning, which does not always seem possible (e.g., DE 4004904). Disassembling must be simple and must not be inconvenient for the patient. In addition, re-assembling after inspection and/or cleaning must not lead to malfunction of the inhaler. One of the consequences of the fine particle adhesion is that most dpi's (dry powder inhalers) with a circulation chamber as disintegration means are not suitable for spherical pellets. For adhesive mixtures, the problem is less extreme, because the larger carrier particles are able to sweep the majority of adhering fines from the inhaler walls.

Although some of the previously reviewed patents refer to a certain residence of the powder inside the de-agglomeration means (e.g. DE 4004904, EP 0407028, DE 4239402, and DE 19522416), for neither of the principles, the possibility of residence time control is mentioned. Only the possibility of residence time variation has been described in DE 19522416, by means of changing the ratio of the rates of the partial air flows through, respectively around the circulation chamber and by altering certain dimensions of the chamber, such as height and diameter.

A few of the previously mentioned patents refer specifically to coarse particle retainment, e.g. GB 1478138, EP 0407028, WO 92/05825, WO 92/04928, EP 0547429, WO 98/26827 and PCT/NL01/00133. The particles with high inertia that are flung outwards by the vortex motion of air within the container described in GB 1478138, circulate along the inner wall of this container. They are unable to pass the narrow tubular extension of the mouthpiece cylinder protruding into the container along the same longitudinal axis of this container. A second coarse particle trap is a narrow tubular passage at the outlet of the mouthpiece cylinder. The cyclone means described in EP 0407028 A2, EP 0547429, WO 98/26827 and PCT/NL01/00133 operate on the basis of the same principle of two competitive forces, being the centrifugal and the drag force. But the concept in WO 92/04928 is basically different, although separation is also upon particle inertia. A separate suction piece, downstream of the whirl chamber, is described in which large particles with high momentum follow a straight path into a dead end tube, whereas the finer particles are dragged by the air stream into a side tube. The separated coarse particles are collected at the bottom of the deadend tube (collection chamber), which must be emptied from time to time. Inertial impaction is also the separation mechanism for impaction jets with different baffles and plates described in WO 92/05825.

Some of the previously mentioned separation principles on the basis of centrifugal flung are described as cyclone means. This is incorrect, because they are not designed to separate all solid material from the airstream, but to classify the airborne particles in two size classes on the basis of their inertia, which means that they are basically air classifiers, as referred to in GB 1478138. However, in none of the patents the cut-off diameters of the classifiers have been mentioned, except for WO 92/05825, providing formulas with experimental constants for the different types of impaction jets. In this patent application it is also explained that the cut-off diameter can be adjusted to suit a particular drug and a particular application.

Only two concepts are known for which the air flow resistance can be controlled within certain limits. In U.S. Pat. No. 5,829,434 it is described that the pressure drop through the swirl nozzle can be changed by varying the cross section for air flow in the passage between the swirl chamber and the chimney. It is stated that the pressure drop through the inhaler should desirably be lower than about 5 kPa for ease of use by patients with impaired respiratory function. For the principle in DE 19522416, it is explained that the inspiratory air stream can be split into a partial flow through the disintegration chamber and a partial flow past this chamber to create a particle free sheath flow around the emitted aerosol cloud. The ratio of these flows can be varied within certain limits without influencing the dose entrainment and the powder disintegration.

SUMMARY OF THE INVENTION

The present invention provides a multifarious disperser for inhalation powders, which can be used in combination with different types of dose systems for the range of dose weights between 2 and 25 mg and different types of powder formulation (with or without carrier excipients). In one particular design, the disperser acts both as a de-agglomeration (disintegration; aerosolization) means and as an air classifier for especially adhesive mixtures. Only fine drug particles are emitted whereas the larger agglomerates and carrier crystals are retained by the disperser. Modification of the basic design enables time controlled release of carrier crystals in these mixtures. In another modification, the concept has optimized performance as disperser in combination with spherical pellets, containing no carrier crystals. Further re-design of the dispersion principle is possible to control the total inhaler resistance and the powder deposition in the upper respiratory tract by means of the addition of a so-called sheath flow of clean air. Modifications also enable carrier retainment in the mouthpiece and elimination of the tangential flow component of the discharge cloud.

Description of the Invention

The concepts described in EP 0547429, DE 19522416 and PCT/NL01/00133 comprise a family of de-agglomeration principles for different applications, all being different modifications of the same basic design. For all concepts, part of the inspiratory air flow is conducted through the dose compartment to entrain the powder. The downstream section of the powder channel, connecting the dose compartment and the de-agglomeration chamber, is tangential to the cylindrical wall of the de-agglomeration chamber. The de-agglomeration chamber has the shape of a disk, sharing its cylindrical axis with the mouthpiece cylinder. A tubular discharge channel, also with the same longitudinal axis, and a much smaller diameter than the de-agglomeration chamber, starts from the center of the cylindrical end of this chamber which is closest to the mouthpiece. Another part of the inspiratory air flow enters the de-agglomeration chamber through tangential slits in its cylindrical wall. The number of these bypass channels may be confined to only one, as for the concept disclosed in PCT/NL01/00133, or there may be more, as in DE 19522416, depending upon the specific application of the de-agglomeration chamber. The partial bypass air flow increases the tangential air and particle velocity inside the chamber. A third part of the inspiratory air flow is not conducted through the de-agglomeration chamber but bypassed towards an annular opening, being co-axial with the discharge channel of the de-agglomeration chamber. The air flow from this annular opening is co-axial with the particle laden air flow from the de-agglomeration chamber, thereby constituting a sheath of particle free air around the aerosol.

Particles circulating inside the de-agglomeration chamber are subjected to three different forces: the drag force of the air, a centrifugal force and the force of gravity. The force of gravity is not relevant to the trajectories of the airborne particles inside the chamber. Particles are flung towards the cylindrical wall of the de-agglomeration chamber as long as the centrifugal force dominates. Whether they roll smoothly along this wall or rattle with only brief moments of contact between the particle and the wall, depends on many factors, such as the load of the de-agglomeration chamber, the number of by pass channels and the particle shape. Also the particle size distribution is important in this respect. If the particles are relatively large, the number of particles inside the de-agglomeration chamber for a certain dose weight is small and the number of particle-to-particle collisions is confined. In addition, the load of the chamber with particles may be rather asymmetrical, depending on the dose weight and the discharge pattern from the powder channel. If on the other hand, the particles are relatively small, the number of particles inside the chamber is much higher, and so will be the number of collisions between the particles, whereas the load may be much more homogeneous, as a large number of particles can be spread out more evenly.

The difference between the concepts disclosed in DE 19522416 and PCT/NL01/00133 is primarily their optimization for a specific application; the concept described in EP 0547429 is the original design without optimization as an integral part of a multiple single dose inhaler for which the individual doses have been weighed into cavities in rotatable disks. The concept in DE 19522416 has been optimized for the de-agglomeration of soft spherical pellets, but this concept serves very well for adhesive mixtures too. The concept described in PCT/NL01/00133 has been designed for adhesive mixtures in applications for which carrier retainment is desired. The reasons for carrier retainment may be different. The possible adverse side effects from substantial drug deposition in the patient's throat have already been mentioned. Released carrier particles do deposit in the throat as a consequence of their large inertia, even at lower flow rates, when they are discharged from the inhaler, and they still carry drug particles on their surface on release. By withdrawing the carrier particles from the inspiratory airstream, throat deposition can be reduced considerably. But also for formulation studies with adhesive mixtures, carrier withdrawal can be valuable. Retained carrier particles can be analyzed upon residual drug content, thus to obtain information about the drug-to-carrier interaction and drug detachment during inhalation. This information is more accurate and reliable than that from collected fine particle fractions in an impactor, which are influenced by irreproducible losses from adhesion onto the inner walls of the inhaler, inlet tube and impactor stages and incomplete collection by the final stage.

The disruption mechanisms for the two types of formulations are basically different for the two de-agglomeration concepts in DE 19522416 and PCT/NL01/00133. As soft spherical pellets roll along the cylindrical wall of a de-agglomeration chamber, they wear mainly by friction. Detached fine particles or small clusters of primary particles either adhere to the wall of the chamber by van der Waals (or Coulombic) forces, or they are dragged by the air stream towards the discharge channel. Because of this fine particle adhesion onto particularly the cylindrical wall of the de-agglomeration principle, the concept disclosed in EP 0547429 can not be used for soft spherical pellets without the addition of (large) so-called sweeper crystals to the formulation, as described in PCT/NL01/00133. Without these sweeper crystals, de-agglomeration of spherical pellets is (near) complete after a certain residence time in the de-agglomeration chamber, but the reduction of the emitted fine particle dose as a consequence of the adhesion onto the inhaler walls is by 50% or even more, depending on the type of drug to be inhaled.

In the concept disclosed in DE 19522416, the number of bypass channels has been increased to seven in order to reduce the surface area of the cylindrical wall by a large number of interruptions and to create a circulation pattern inside the chamber that forces the pellets to collide with the remaining sections of the cylindrical wall at angles that are more obtuse than the angle between two neighboring sections of this wall. Instead of rolling along a continuous cylindrical chamber wall, the pellets are constantly traversed by the 'air barrier' between the pellets and the remaining sections. They rather skim than strike these sections, and as a result of the strongly reduced contact area, the fine particle adhesion onto the cylindrical wall is minimized. De-agglomeration is mainly by shear of the bypass flows. As pellets approach the next section of the cylindrical chamber wall, they enter the region in which a bypass flow intersects their trajectory at an angle of 45 degrees. As a result of the high air velocity through the bypass channels, which is approximately 10 m/s at a flow rate of 60 l/min through the inhaler, the relatively weak pellets are disrupted into smaller fragments and eventually break-up in primary particles or small clusters, that are fine enough to be dragged into the discharge channel.

In contrast, carrier particles in adhesive mixtures that circulate in the concept disclosed in PCT/NL01/00133, bounce off the cylindrical wall after collision against it as a result of their irregular shape, which prevents them to roll smoothly like spherical pellets. There trajectory can best be described as a pathway along neighboring parabolas, all lying in the same plane being perpendicular to the cylindrical axis of the de-agglomeration chamber, with their tops directed to the center of this chamber. After bouncing off the wall, the particles are forced back towards the periphery of the de-agglomeration chamber by the action of the centrifugal force, in order to encounter a next collision.

Meanwhile the particles travel in tangential direction through the chamber. On impact, fine drug particles are detached from the carrier crystals, depending upon the angle and velocity of the collision with the wall. In the basic concept disclosed in EP 0547429 and PCT/NL01/00133, there are only two interruptions in the cylindrical wall of the de-agglomeration chamber. As a consequence, there is little disturbance of the particle trajectories and particles above the cut-off diameter at the given inspiratory flow rate are retained with quite high efficiency. The tops of the parabolas are only at a small distance from the cylindrical wall of the chamber, because the angle of collision is quite obtuse. Therefore, a certain distance between the bouncing particles and the discharge channel is maintained, even when the particles are at the top of a parabola. The extension of the discharge channel inside the de-agglomeration chamber contributes to the nearly complete large particle withdrawal by reducing the cross section of the passage between the circulation chamber and the discharge channel. In this basic modification, the circulation chamber acts both as a de-agglomeration means and as an air classifier. FIG. 1 shows the carrier withdrawal efficiency of an air classifier concept similar to the concept disclosed in PCT/NL01/00133 for different narrow size fractions of crystalline alpha lactose monohydrate at a low flow rate of 30, respectively 40 l/min. Only for fractions with a median diameter smaller than 50 $\mu$m, the efficiency is less than 90%. The nominal cut-off diameters for colistin sulfate (for a sample with a size distribution between 0.7 and 87 $\mu$m) in the same classifier, as derived from laser diffraction measurement of the aerosol cloud using a special inhaler adapter, are shown in FIG. 2. With increasing flow rate, not only does the mean cut-off diameter decrease, but also the spread between the individual inhalations.

The interruptions in the cylindrical wall of the de-agglomeration chamber, the many bypass flows intersecting the particle trajectories as well as the removal of the extension of the discharge tube projecting into the de-agglomeration chamber in concept DE 19522416, influence the carrier bounce trajectories. The angles of impact are slightly more acute, the flow pattern inside the de-agglomeration chamber is more turbulent and the cross section of the passage between the circulation chamber and the discharge channel is increased. As a result, carrier particles are able to enter the discharge channel and a gradual emptying of the circulation chamber is obtained. As may be expected, the average carrier residence time increases with increasing flow rate for a certain carrier size fraction, because of increasing centrifugal forces, which keep the particles in circulation. But the flow rate dependence decreases with increasing mean carrier size; for carrier particles with a mass median diameter above 150 $\mu$m, the flow rate effect is subordinate within the range between 30 and 90 l/min. Residence time decreases with increasing mean carrier diameter, because the variation in particle bounce trajectories becomes greater with increasing particle inertia and shape deviation. Larger lactose carrier particles tend to have a much more irregular shape than finer crystals, even if they are from the same batch of lactose, and the correcting effect of the drag force exercised by the tangential air flow inside the circulation chamber diminishes with increasing particle inertia. As a consequence of the gradual carrier particle release, the average residence time of these particles in concept DE 19522416 is generally lower than the total inhalation time. And as a result of that, the fine particle detachment for the same adhesive mixture is less complete than the degree of removal obtained with the concept according to PCT/NL01/00133, having the benefit of near-complete carrier withdrawal.

Most characteristic for the invention are (a) splitting of the inspiratory air stream into three different partial flows, and (b) the presence of a disk-shaped circulation chamber, which combination provides the possibilities for: creating a sheath of particle free air around the aerosol cloud to reduce mouth deposition from spherical pellets, controlling the inhaler resistance within a range that is comfortable for the patient and favorable in respect of drug deposition in the upper respiratory tract, creating an air barrier inside the de-agglomeration chamber which diminishes fine particle adhesion onto the inner walls of this chamber in case of de-agglomeration of spherical pellets, imposing a certain residence time on large carrier crystals in the de-agglomeration chamber to improve utilization of the available energy for fine particle detachment, classifying of the particles in a size fraction that is favorable for deposition in the lower respiratory tract (to be released) and a fraction that is too coarse to enter the site of action (to be retained), and deposition of large particles in the front of the patient's mouth instead of in the throat, by the tangential flow component in the discharge cloud from the inhaler, as a consequence of which large particles are immediately flung sideways after leaving the mouthpiece. This enables the patient to rinse the mouth after inhalation and to avoid systemic or local side effects from this part of the dose.

Two further aspects of the invention are the desired duration of the carrier residence in the de-agglomeration means, and the possibility to control the residence time in the de-agglomeration chamber accordingly.

For the control of the residence time, another concept with improved de-agglomeration efficiency for adhesive mixtures has been developed, as will be described hereafter as another new aspect of the invention. A further aspect disclosed hereafter, is the modular construction of the de-agglomeration means which enables the exchange of different concepts within the same dry powder inhaler, dependent on the type of formulation to be used and/or special requirements, such as a specific air flow resistance for a particular group of patients or complete carrier retainment.

In its various aspects the invention provides a disintegration means for dry powder inhalers, comprising a substantially cylindrical air circulation chamber with a height being smaller than its diameter, and at least two air supply channels which enter the chamber as tangents to its cylindrical wall at generally opposite sides of this wall, suitable for creating a circular air flow pattern inside the chamber, both air channels either having different inlets or alternatively sharing the same inlet which is split up, so as to have one passageway for traversing the dose measuring or dose supplying region of the inhaler for enabling the powder quantity of a single dose dragged into the circulation chamber by air flowing through this passageway, and the other passageway to serve as a bypass channel towards the circulation chamber suitable for accelerating the particles and creating a more symmetrical flow pattern inside said chamber; a disintegration means for dry powder inhalers comprising a tubular discharge channel having approximately the same longitudinal axis as the circulation chamber but a much smaller diameter and an extension of this channel protruding into said chamber over a length being smaller than the total height of the circulation chamber; a disintegration means for dry powder inhalers comprising a third air passageway in addition to both previously mentioned air supply channels for the circulation chamber, either with a separate inlet channel or as a branching of the cyclone bypass channel, through which the air flow, being part of the total inspiratory flow, is controllable by means of an air flow constriction, and which passageway ends in an annular opening between the discharge channel of the circulation chamber and a co-axial mouthpiece cylinder with larger inner diameter than the discharge channel, for controlling the total air flow resistance of the inhaler device and for creating a sheath of clean air around the aerosol cloud which reduces the mouth deposition of drug particles released from spherical pellets which is a consequence of return flows occurring in the mouth during inhalation through an inhaler with tubular mouthpiece cylinder typically having a smaller diameter than the height or width of the mouth cavity; a disintegration means for dry powder inhalers comprising more than one, preferably seven, air supply channels for the bypass flow, all being substantially symmetrically distributed over the circumference of the cylindrical wall of the circulation chamber, in addition to the channel traversing a dosing compartment of the inhaler, when in use, providing a so-called air barrier between the circulating particles and the interior wall of the chamber created by air flows through the bypass channels that are closely adjacent to each other, as well as a reduced surface area of said wall, providing in combination a strongly reduced fine particle adhesion onto said wall, especially for the combination with soft spherical pellets; a disintegration means for dry powder inhalers, wherein obtuse angles of about 135 degrees between the remaining sections of the cylindrical wall are provided by the air supply channels entering the circulation chamber, which in use provide an increase of the angle of impact and cause particles to bounce off these wall sections of the chamber towards the center of this chamber over a larger distance allowing carrier particles to approach or cross the central area of the circulation chamber from which they can enter the discharge channel, which results in a gradual release of carrier particles from the circulation chamber through said discharge channel; a disintegration means for dry powder inhalers wherein a top end of the circulation chamber on its discharge channel side forms a top plate of said chamber, which has a larger diameter than the external diameter of the chamber itself, thereby creating a circular flange that stands out from the external cyclone wall and blocks a passageway for air through an annular channel between the cylindrical circulation chamber and the co-axial tubular mouthpiece cylinder with larger diameter by making contact with the interior wall of said mouthpiece cylinder, except for some small interruptions in said flange that control the air flow resistance of this passageway, adapted to a predetermined total resistance of the circulation chamber for controlling the partial sheath flow through the annular opening between the co-axial mouthpiece cylinder and discharge channel of the circulation chamber further downstream of this flange; a disintegration means for dry powder inhalers wherein the number of bypass channels is between one and eight, preferably three, preferably being substantially symmetrically distributed over the circumference of the wall of the circulation chamber, in addition to the channel traversing the dosing means of the inhaler, and the shape of the circulation chamber is cornered, preferably eight-cornered, having sections of the wall of the chamber of different lengths, wherein longer sides and adjacent shorter sides alternate, the longer sides serving as acceleration sides along which particles gain rate of movement to increase the impact velocity, and the shorter sides having preferably obtuse angles of about 135 degrees with the longer sides, being suitable as impact sites; a disintegration means for dry powder inhalers wherein a tubular discharge channel has different inner diameters over its length to control the area inside the circulation chamber from which carrier particles may enter this channel and such to control the discharge rate of a carrier dose with defined size distribution from the circulation chamber, and more particularly, to control the average carrier residence time inside the circulation chamber which determines the degree of fine particle detachment from the carrier and thus, the emitted fine particle dose at a certain inspiratory flow rate; a disintegration means for dry powder inhalers comprising longitudinal ridges or strips on the inner tubular wall of the discharge channel or a framework formed inside said channel likewise from wall to wall which, in cross section, has preferably the shape of a cross dividing the discharge channel in about four longitudinal sections, said ridges or framework provide a flow correcting effect by the elimination of the tangential flow component for particles travelling through the tubular discharge channel, thereby causing these particles to be discharged substantially in longitudinal direction instead of being flung sideways by centrifugal action; a disintegration means for dry powder inhalers comprising two concentric annular channels between the mouthpiece cylinder and the discharge channel, one channel serving as an air passageway for the bypass flow towards the disintegration means and the sheath flow; the other channel serving as an internal storage room for retained carrier particles, and said mouthpiece cylinder being displaceable in longitudinal direction relative to the discharge channel so as to open the carrier storage chamber during inhalation or to close this chamber after inhalation has been completed for use in combination with concepts of the disintegration means that have not been designed for carrier retainment themselves; a disintegration means for dry powder inhalers wherein the entries of the supply channels into the circulation chamber each having substantially rectangular cross sections; a disintegration means for dry powder inhalers having essential dimensions adapted to an inhaler system so that various embodiments of the disintegration means are easily interchangeable within the same dry powder inhaler system, thus to comprise a modular system that can be adapted to the specific requirements of the powder formulation used in the inhaler; and a disintegration means for dry powder inhalers comprising mechanical coding means interacting with corresponding mechanical coding means in the sense of an antagonist-receptor function between the dose system and the disintegration chamber, to allow attaching of the disintegrating means only to predetermined dosing systems or inhalers to ensure correct combinations between the disintegration means and a predetermined medical powder formulation.

In a further aspect the invention relates to an inhaler comprising a disintegration means as described herein.

In a further aspect of the invention is provided a multifarious and multi purpose disintegration method for dry powder inhalers, for breaking up powdered, binderless drug formulations during inhalation by the patient through the inhaler after previous activation of a single dose, in a weight range between approximately 2 and 25 mg, thus, to release a substantial amount of fine drug particles for deep lung deposition from these formulations, which contain the drug in micronized form, preferably in the size range between 1 and 5 μm, and mostly, but not necessarily, a filling or carrier excipient, having either approximately the same size distribution as the drug in so-called soft spherical 15 pellets, also referred to as soft spherical agglomerates, or comprising much larger crystals that carry the drug particles as primary entities or as small clusters in homogeneous distribution on their surface, attached by mild interaction forces such as van der Waals forces, in so-called adhesive, interactive or ordered mixtures, in which each carrier particle with adhering drug particles can also be considered an agglomerate.

In another aspect of the invention the method comprises that the agglomerates collide repeatedly with the cylindrical wall of the circulation chamber and/or with each other while they circulate inside the chamber, so that drug particles are detached from these agglomerates by impact and shear forces.

In yet another aspect of the invention the method comprises that separation of particles upon their difference in inertia takes place by the action of drag and centrifugal forces, the larger particles subjected to predominant centrifugal force being retained in the chamber and the smaller particles subjected to predominant drag force being released with the inspiratory air, as a result of which the circulation chamber acts not solely as a break-up chamber for the drug agglomerates but also as an air classifier, to provide substantial reduction of drug deposition in the mouth and throat from drug not being detached from the carrier crystals or being disintegrated insufficiently as well as the advantage of reduced powder administration to the patient which minimizes irritant mouth feel and chest tightness.

In another aspect of the invention the method comprises that the inhaler discharge cloud has a strong tangential flow component, which causes larger particles, such as carrier particles that are unable to reach the target area in the lungs, to fling sideways by centrifugal action immediately after discharge from the mouthpiece of the inhaler, thereby causing these particles to deposit in the front of the mouth of a patient instead of in the throat, thereby reducing adverse local side effects in the throat, like hoarseness or Candidiasis connected to the use of cortico steroids, from drug deposition of particles that have not been detached from the carrier particles, and providing for facilitated removal of these carrier particles by mouth rinsing.

The desired duration of the carrier circulation in a de-agglomeration chamber depends on the rate with which the drug particles can be detached from the carrier crystals in this chamber. The basic air classifier disclosed in PCT/NL01/00133 provides the possibility to study this detachment rate. Carrier crystals that are retained by this classifier can be analyzed upon residual drug (CR: carrier residue) after inhalation as function of the inhalation (circulation) time. Carrier residues (as percent of initial drug load) for mixtures of 0.4% budesonide with three different carrier fractions in this air classifier concept are shown in FIG. 3A for the inspiratory flow rate of 60 l/min (equals 9.3 kPa). The carrier fractions used were 45–63 μm, resp. 150–200 μm from Pharmatose 150 M (DMV International, The Netherlands) and 150–200 μm from Capsulac 60 (Meggle GmbH, Germany). Because a minor carrier passage occurred (FIG. 1), all carrier residue values have been extrapolated to 100% carrier withdrawal. Two different mixing times were used: 10 and 120 minutes in a Turbula mixer at 90 r.p.m. (W. A. Bachofen, Switzerland). The release curves (100 minus CR) for the mixtures after 10 minutes mixing time are presented in FIG. 3B.

In one embodiment, the invention of the present application provides a dry powder inhaler having a circulation chamber wall, a top wall and a bottom wall which together define a circulation chamber having a central axis. A distance between the top and bottom walls defines a chamber height and the circulation chamber wall defines a circumference of the circulation chamber and a chamber diameter. The chamber height is less than the chamber diameter. A first supply channel defines a first opening in the circulation chamber wall, is in communication with a powder supply region and conveys air and powder to the circulation chamber in a direction substantially tangential to the circumference of the circulation chamber. A plurality of second air supply channels each define a second opening in the circulation chamber wall with the second openings and the first opening being positioned substantially symmetrically about the central axis. Each second air supply channel is in communication with a source of air wherein each second air supply channel conveys substantially powder-free air to the circulation chamber. Each second air supply channel is oriented to direct conveyed air into the circulation chamber in a direction substantially tangential to the circumference of the circulation chamber. The first supply channel and each of the second air supply channels are oriented to convey air into the circulation chamber in a common rotational direction about the central axis whereby air and powder are conveyed within the circulation chamber in a generally circular flow pattern. A discharge channel is positioned substantially coaxially with the circulation chamber and has a first end and an opposite second end. A portion of the discharge channel extends through the top wall and the first end defines an inlet positioned within the circulation chamber between the top wall and bottom wall. The discharge channel portion disposed within the circulation chamber has an outer perimeter spaced radially inwardly from the circulation chamber wall. The second end defines a discharge opening. A third air supply channel is in communication with a source of air and conveys substantially powder-free air. The third air supply channel defines an outlet positioned coaxially with the second end and forms an annular opening surrounding an exterior surface of the discharge channel at the second end. The third air supply channel thereby provides a sheath of powder-free air surrounding the powder-laden air discharged from the second end. In one alternative of such an embodiment of the invention, the plurality of second air supply channels may comprise seven second air supply channels. The first opening and the second opening may also be configured whereby the openings each have a top edge positioned adjacent the top wall and a bottom edge positioned approximately midway between the top wall and bottom wall and the discharge channel may extend into such a circulation chamber by a distance whereby the inlet is positioned closer to the bottom wall than to the top wall. The top wall may also include a flange which extends radially outwardly of the circulation chamber wall and defines passages extending through the flange which form a portion of the third air supply channel.

In another embodiment, the invention of the present application provides a dry powder inhaler which includes a circulation chamber wall, a top wall and a bottom wall which together define a circulation chamber having a central axis. A distance between the top and bottom walls defines a chamber height and the circulation chamber wall defines a circumference of the circulation chamber and a chamber diameter. The chamber height is less than the chamber diameter. A first supply channel defines a first opening in the circulation chamber wall and is in communication with a powder supply region whereby the first supply channel conveys air and powder to said circulation chamber. The first supply channel is oriented to direct conveyed air and powder into the circulation chamber in a direction substantially tangential to the circumference of the circulation chamber. At least one second air supply channel defines at least one second opening in the circulation chamber wall. The at least one second opening and the first opening are positioned substantially symmetrically about the central axis. The at least one second air supply channel is in communication with a source of air wherein the at least one second air supply channel conveys substantially powder-free air to said circulation chamber. The at least one second air supply channel is oriented to direct conveyed air into the circulation chamber in a direction substantially tangential to the circumference of the circulation chamber. The first and second air supply channels are oriented to convey air into the circulation chamber in a common rotational direction about the central axis whereby air and powder are conveyed within the circulation chamber in a generally circular flow pattern. A discharge channel is positioned substantially coaxially with the circulation chamber and has a first end and an opposite second end. The first end defines an inlet in communication with the circulation chamber and the second end defines a discharge opening for discharging powder-laden air. The circulation chamber wall is defined by a plurality of wall segments, each of the wall segments being substantially planar and having a height extending from said bottom wall to said top wall. The plurality of wall segments comprise a plurality of long wall segments and a plurality of short wall segments wherein each of the long wall segments have a length no less than a first length and each of said short wall segments have a length no greater than a second length. The first length is greater than the second length. The long wall segments and the short wall segments are alternatively positioned along the circumference of the circulation chamber and one of the short wall segments is positioned at an angle to and, with respect to the circular flow pattern, downstream of each of the long wall segments. In one alternative of such an embodiment, the at least one second opening may include 3 to 8 second openings positioned substantially symmetrically about the central axis and oriented to direct powder-free air into said circulation chamber in a direction substantially tangential to an interior surface of said circulation chamber wall and in the common rotational direction and wherein the plurality of long wall segments is equal in number to a total number of the second openings and the first opening, and the plurality of short wall segments is equal in number to the total number of said second openings and said first opening. For example, such an alternative embodiment having 3 second openings would have 4 long wall segments and 4 short wall segments.

In yet another embodiment, the invention of the present application provides a dry powder inhaler having a circulation chamber wall, a top wall and a bottom wall which together define a circulation chamber having a central axis. A distance between the top wall and the bottom wall defines a chamber height and the circulation chamber wall defines a circumference of the circulation chamber and a chamber diameter. The chamber height is less than the chamber diameter. A first supply channel defines a first opening in the circulation chamber wall and is in communication with a powder supply region whereby the first supply channel conveys air and powder to said circulation chamber. The first supply channel is oriented to direct conveyed air and powder into the circulation chamber in a direction substantially tangential to the circumference of the circulation chamber. A plurality of second air supply channels define a plurality of second openings in the circulation chamber wall. The second openings and the first opening are positioned substantially symmetrically about the central axis. The second air supply channels are in communication with a source of air wherein the second air supply channels convey substantially powder-free air to the circulation chamber. Each of the second air supply channels is oriented to direct conveyed air into the circulation chamber in a direction substantially tangential to the circumference of the circulation chamber. The first supply channel and each of the second air supply channels are oriented to convey air into the circulation chamber in a common rotational direction about the central axis whereby air and powder are conveyed within the circulation chamber in a generally circular flow pattern. A discharge channel is positioned substantially coaxially with the circulation chamber and has a first end and an opposite second end. The first end defines an inlet in communication with the circulation chamber and the second end defines a discharge opening for discharging powder-laden air. The circulation chamber wall is defined by a plurality of wall segments, each of the wall segments are substantially planar and have a height extending from the bottom wall to the top wall. The wall segments are all positioned in pairs wherein each such pair comprises two intersecting wall segments forming an angle of approximately 135 degrees. The first opening and the second openings are positioned to separate each such pair of wall segments from an adjacent one of the pairs of wall segments.

In a further embodiment, the present invention provides a dry powder inhaler which includes a circulation chamber wall, a top wall and a bottom wall which together define a circulation chamber having a central axis. A distance between the top and bottom walls define a chamber height and the circulation chamber wall defines a circumference of the circulation chamber and a chamber diameter. The chamber height is less than the chamber diameter. A first supply channel defines a first opening in the circulation chamber wall and is in communication with a powder supply region whereby the first supply channel conveys air and powder to the circulation chamber. The first supply channel is oriented to direct conveyed air and powder into the circulation chamber in a direction substantially tangential to the circumference of the circulation chamber. At least one second air supply channel defines at least one second opening in the circulation chamber wall with the second openings and the first opening positioned substantially symmetrically about the central axis. The second air supply channel is in communication with a source of air wherein the second air supply channel conveys substantially powder-free air to the circulation chamber. The second air supply channel is oriented to direct conveyed air into the circulation chamber in a direction substantially tangential to the circumference of the circulation chamber. The first supply channel and the at least one second air supply channel are oriented to convey air into the circulation chamber in a common rotational direction about the central axis whereby air and powder are conveyed within the circulation chamber in a substantially circular flow pattern. A discharge channel is positioned substantially coaxially with the circulation chamber and extends from a first end to an opposite second end. The discharge channel extends through the top wall and the first end defines an inlet positioned within the circulation chamber between the bottom wall and the top wall. The portion of the discharge channel disposed within the circulation chamber has an outer perimeter spaced radially inwardly from the chamber wall. The second end defines a discharge opening. The discharge channel has an interior surface defining a substantially circular cross sectional shape. A baffle member is positioned in the discharge channel to disrupt helical flow of particles through the discharge channel and direct particles in a direction substantially parallel to the central axis. In one alternative of such an embodiment, the baffle member comprises a plurality of ridges projecting radially inwardly from the interior surface of the discharge channel and extending parallel to the central axis wherein the ridges project a distance less than the diameter defined by the interior surface. In another alternative of such an embodiment, the baffle member comprises a plurality of baffle frameworks extending between diametrically opposite sides of the interior surface of the discharge channel with each of the frameworks being positioned at spaced locations along the central axis. Such frameworks may be cross-shaped.

In still another embodiment, the invention of the present application provides a modular dry powder inhaler system which includes an inhaler body having a circulation chamber wall and a bottom wall. The chamber wall and bottom wall define a portion of a circulation chamber which has a central axis. The circulation chamber wall also defines a circumference of the circulation chamber. A first supply channel defines a first opening in the circulation chamber wall and is in communication with a powder supply region whereby the first supply channel conveys air and powder to the circulation chamber. The first supply channel is oriented to direct conveyed air and powder into the circulation chamber in a direction substantially tangential to the circumference of the circulation chamber. At least one second air supply channel is provided and defines at least one second opening in the circulation chamber wall wherein the at least one second opening and the first opening are positioned substantially symmetrically about the central axis. The at least one second air supply channel is in communication with a source of air wherein the at least one second air supply channel conveys substantially powder-free air to the circulation chamber. The at least one second air supply channel is oriented to direct conveyed air into the circulation chamber in a direction substantially tangential to the circumference of the circulation chamber. The first and second air supply channels are oriented to convey air into the circulation chamber in a common rotational direction about the central axis whereby air and powder are conveyed within the circulation chamber in a substantially circular flow pattern. Also included in the system are a plurality of top plates, each of the top plates is removably mountable to the inhaler body and forms a top wall of said circulation chamber when mounted thereto. A distance between the top and bottom walls defines a chamber height and the circulation chamber wall defines a chamber diameter with the chamber height being less than the chamber diameter. The top plates also each define a discharge channel which is positionable substantially coaxially with said circulation chamber. The discharge channels each have a first end and an opposite second end. The first ends define an inlet opening in communication with the circulation chamber and the second ends define a discharge opening for discharging powder-laden air. The plurality of top plates have a plurality of different configurations whereby a selected one of the top plates can be attached to the inhaler housing based upon user requirements. In one alternative of such an embodiment, the system also includes a mouthpiece removably mountable to the inhaler body. Attachment of the mouthpiece secures a selected one of the top plates to the inhaler body. The mouthpiece also defines a third air supply channel in communication with a source of air wherein the third air supply channel conveys substantially powder-free air. The third air supply channel also defines an outlet positioned coaxially with the second end wherein the outlet forms an annular opening surrounding an exterior surface of the discharge channel at the second end and whereby the third air supply channel supplies a sheath of powder-free air surrounding the powder-laden air discharged from the second end. In another alternative of such an embodiment, each of the top plates define a discharge channel wherein each of the second ends have a common discharge opening diameter and the first ends define a plurality of different inlet opening diameters.

FIG. 3A shows that the carrier residue after 10 minutes mixing time (open symbols) decreases most strongly in this type of classifier within the first halve second of inhalation, towards approximately 50% of the initial carrier load. In the following 1.5 s, another 20 to 25% of the drug is detached and the carrier residue is further reduced to about 30% (after 2 s total inhalation time). And even after 6 seconds inhalation, the endpoint has not yet been achieved, which seems to be around 10% of the initial drug load. The results prove that the differences between the different carrier fractions are not dramatic for this type of classifier (at 60 l/min).

FIG. 3A also shows that an increase in mixing time decreases the rate of drug particle detachment. For example, the mean carrier residue (for all three carrier fractions), after one second of circulation in the classifier, increases from 42% to 70% as a consequence of an increase in mixing time from 10 to 120 minutes. And in terms of the same degree of detachment: the effect of 0.5 s circulation time after 10 minutes mixing equals that of a circulation time of nearly 3 seconds after 120 minutes mixing time. These results are in agreement with the total mixing concept introduced by Staniforth, J. N. Order out of chaos. J. Pharm. Pharmacol. 39 (1987) 329–334, meaning that there is an ongoing drug agglomerate break-up during mixing which results in a gradual change from predominant cohesion between drug particles towards predominant adhesion between primary drug and carrier particles with increasing mixing time. This, in combination with another theory, stating that removal forces during inhalation can get better hold of larger drug agglomerates than of primary drug entities Aulton, M., Clarke, A. Powder Technology and Powder Characterization in Dry Powder Inhalation Systems. In: Pharmaceutical Aerosols and Dry Powder Systems. Proceeds of the Eur. Continuing Education College, London, November 1996, explains the decrease in rate of fine drug particle detachment caused by an increased mixing time for the powder.

The basic air classifier described in PCT/NL01/00133 is a highly effective de-agglomeration principle compared to most marketed dry powder inhalers, and so are the concepts described in DE 19522416 and EP 0547429. This is shown in FIG. 4, presenting the fine particle fractions from these concepts and some marketed devices, at 4 kPa pressure drop across these devices, collected in a cascade impactor for adhesive mixtures with different drugs and different types of carrier material. CII represents a basic classifier of the type disclosed in PCT/NL01/00133 (the same as used for FIGS. 3A and B), whereas the Novolizer is the marketed version of the concept presented in DE 19522416. The fine particle fractions obtained with CII are from mixtures with 0.4% budesonide and the marketed Pharmatose types of carrier mentioned in the figure. The results obtained with the Novolizer are for mixtures with 1% budesonide or 1% salbutamol sulfate and carrier materials mentioned in the legend of this figure. For the marketed dpi's, also two different formulations were tested (see legend). All inhalation times were 3 seconds. The average fine particle fractions obtained with CII and the Novolizer are on average about twice as high as those obtained with the marketed dpi's at the same pressure drop through the inhalers.

Possible explanations for the differences between the fine particle fractions from the marketed inhalers and the air classifiers in the test inhaler CII and the Novolizer are (a) different efficiencies in utilizing the available energy from inspiration through the device and (b) different properties for the formulations used, which contain standard lactose products for CII and the Novolizer. The amount of energy (Nm) that is available for powder disintegration can be calculated by multiplying the average pressure drop across the inhaler (Nm$^{-2}$) by the average volumetric air flow rate through the device (m$^3$s$^{-1}$) and the duration of the inhalation manoeuvre (s). Different efficiencies in powder break-up may be the result of (a) different energy dissipation rates (Nms$^{-1}$) and/or (b) different durations of energy consumption (s) for the de-agglomeration process; the latter being the result of different residence times for the powder inside the inhaler device. It is quite obvious that for inhalers with a lower energy dissipation rate than the classifier used for FIGS. 3A and B, the drug detachment rate will also be lower. This means that a longer residence time will be necessary to obtain the same degree of fine particle detachment from the carrier crystals. If on the other hand, the energy dissipation rate can be increased, the residence time may be reduced, which reduces the hazard of incomplete dose inhalation for patients that are unable to sustain the necessary inhalation manoeuvre for a certain duration.

Recent regulatory directives prescribe that the complete dose can be inhaled within 2 liters. This demand confines the residence time for the dose in the de-agglomeration chamber to 2 seconds at an average flow rate of 60 l/min. Considering furthermore the need for a certain volume of air to transport the detached fine drug particles to the site of action in the respiratory tract, drug particle detachment should preferably be 'completed' within the first 1 to 1.5 s from the start of the inhalation manoeuvre at this flow rate. These limitations for an air classifier as disclosed in PCT/NL01/00133 include that only approximately 60 to 65% of the dose can be detached from carrier materials as used in the experiments for FIGS. 3A and B (which is about 70% of the maximal attain able release from these carriers). This explains why a further increase of the energy dissipation rate for powder break-up (Nm.s$^{-1}$) has been an important aspect for this invention.

Control of the residence time inside the circulation chamber can be obtained by (a) selecting the appropriate carrier size distribution for the adhesive powder mixture, (b) confining the rate of attainable flow rates through the inhaler device and (c) varying the diameter of the discharge channel of the circulation chamber. An example of the effect of the mean carrier diameter and of the inspiratory flow rate on the residence time in a particular circulation chamber of the type described hereafter, is given in FIG. 5. The data have been obtained by measurement of the pressure drop reduction across the means, which is a consequence of the presence of particles in the chamber. Without particles, the turbulence of the air circulating inside the chamber is much higher than that for a particle laden circulation chamber at the same flow rate. Particles smoothen the flow pattern inside the chamber by their much higher inertia compared to that of the air. Consequently, the pressure drop through the chamber is lower in the presence of particles. The difference can be measured as function of the inhalation time. When the reduction is reduced to zero, all particles have passed the chamber, as has been checked by inspection of the circulation chamber after completion of the inhalation, as well as by optical concentration measurement of the discharge cloud from the inhaler with laser diffraction technique during inhalation.

For particles larger than 125 μm, the effect of flow rate is nearly negligible in the concept used for preparation of FIG. 5. Moreover, the residence time for such particles in this concept is in agreement with the desired range up to 1.5 s, as discussed previously. This is the result of the predetermined design and dimensions of the de-agglomeration principle. The effect of flow rate increases with decreasing mean carrier size and results in a maximum value of more than 3 seconds for this particular concept at 90 l/min. For much lower flow rates, the residence time is nearly independent of the carrier size distribution.

A better control of the residence time can be obtained by varying the diameter of the discharge channel of the circulation chamber. This is shown in FIG. 6 for the same concept as used for the experiments in FIG. 5, with two different diameters: 7 and 8 mm. The open symbols in this figure represent marketed lactose products with a relatively wide size distribution, whereas the closed symbols are for narrow fractions derived from Pharmatose 110M. The average reduction in residence time for products with a mean diameter of 150 pm (or more) from increasing the diameter of the discharge channel from 7 to 8 mm is nearly by 50% for this type of circulation chamber (at 60 l/min). These are only examples that elucidate (a) the many possibilities for control of the residence time in this type of de-agglomeration chamber and (b) the range of times within which the particle circulation inside this chamber can be varied.

In addition to all previously mentioned effects, there may be an effect of drug load on the carrier residence time inside the circulation chamber, as shown (as an example) for three different carrier materials and two different drug loads in FIG. 7, for the same concept as used for FIGS. 5 and 6, with 7 and 8 mm discharge channels (dose weight is approximately 14 mg). The effect of drug load on the residence time for the carrier fraction is quite small for carriers with a relatively large diameter, but for much smaller particles, the effect can be quite substantial. The reason for the elongation of the residence time is an increase in inertia of the circulating air inside the de-agglomeration chamber by the dispersion of detached fine particles into the air. As a result of this higher inertia for the aerosol compared to particle free air, carrier particle pathways inside the chamber can be better re-directed to the original circular motion after there has been a scattering in other directions from collisions of carrier particles with the inhaler walls and/or with each other. The correction efficiency is highest for the smallest carrier crystals, having the lowest inertia themselves. The effect decreases with increasing diameter for the discharge channel: already for a concept with 8 mm channel, the effect has been diminished, even for the 63–100 μm fraction.

All previously mentioned variables that influence the residence time of the formulation inside the circulation chamber can be controlled, except for the inhalation manoeuvre by the patient. However, by selecting the appropriate size distribution for the carrier material, the effect of inspiratory flow rate can be minimized (FIG. 5). The use of relatively large carrier materials is not problematic from the viewpoint of fine drug particle detachment for the type of de-agglomeration principle disclosed hereafter. This, in contrast with many other principles, as discussed previously. This may become clear from the FIGS. 3 and 4. The fractions 150–200 μm in FIG. 3 exhibit the same fine particle detachment rate towards also the same end value as the much finer fraction 45–63 μm (at 60 l/min). The median diameters (from dry laser diffraction analysis) for Pharmatose 110M and Capsulac 60 in the mixtures presented in FIG. 4 are approximately 130 μm ($X_{100}$=365 μm), respectively 190 μm ($X_{100}$=360 to 460 μm), depending upon the batch. A larger diameter is even preferable from the viewpoint of dose reproducibility.

The residence times measured with the differential pressure drop reduction method equal the times necessary for complete carrier discharge from the circulation chamber. Because the passage of the carrier particles is more or less gradual from the start of the inhalation, the average residence time in the circulation chamber is much shorter. If inhalation of the total dose should be within 2 liters, total carrier passage should preferably be completed within 1,5 liter in order to have some volume (0.5 liter) left for fine particle transport to the site of action. Accordingly, the average residence time in the de-agglomeration chamber is much shorter than 1.5 s at 60 l/min (in case of a perfectly constant discharge rate about 0.75 s).

From FIG. 3, it can be concluded that fine particle detachment after 0.75 s is only approximately 60% of the dose (for the already highly efficient basic air classifier in PCT/NL01/00133 and rather common carrier materials as Pharmatose or Capsulac fractions). This includes that 40% of the dose is wasted by joined deposition with the carrier crystals in the patient's mouth and throat. This part of the dose has the possibility to cause adverse local side effects on these sites. From the released 60% of the drug dose, a certain amount is also lost by inhaler and mouth accumulation, meaning that less than half the dose is available for entering the target area, providing that all drug particles (or small agglomerates) within this part of the dose have the correct size distribution. This is an argument for further improvement of the concept. One possibility to increase the fine particle output from an inhaler is to optimize the powder formulation with respect to carrier properties and mixing time (e.g., FIGS. 3A and 3B). This approach lies without the scope of this invention. Another way is to increase the inhaler's efficiency in terms of energy dissipation rate for powder de-agglomeration. This improvement of the inhaler's efficiency for adhesive mixtures is one aspect of this invention, as already been mentioned previously.

Within the same circulation time, the efficiency of fine particle detachment from hosting carrier crystals inside a circulation chamber can be increased by (a) increasing the carrier particle velocity on impact, (b) increasing the number of collisions within said circulation time and (c) optimizing the angle of impact. The particle velocity on impact depends not solely on the air velocity inside the circulation chamber but also on the time available between two collisions to re-accelerate the particle by the drag force. When carrier particles collide with the inhaler wall, they need to loose part of their momentum in order to generate inertial, and more specifically, deceleration forces acting on adhering drug particles. For the necessary acceleration time between collisions, (a) the residual velocity (in the new direction) after collision, (b) the distance between two collision zones, (c) the air velocity inside the chamber and (d) the particle mass are most relevant. And for the residual velocity after impact towards the next collision zone, the angle of impact is of importance too.

The cylindrical wall of the circular chamber disclosed in PCT/NL01/0013330 has only two disturbances from air channels. For particles circulating in this chamber, the angle of collision with this cylindrical chamber wall is quite obtuse. Therefore, the loss of momentum on impact is not extreme and as a result, the residual velocity is quite high. Particles circulate within this chamber with high velocity when the air velocity is high and in addition to that, the number of collisions per unit time is quite high too. High velocity and high number of collisions compensate for the rather obtuse angle of impaction. And because there is no carrier passage, energy consumption for fine particle detachment is for the whole duration of the inhalation and this makes the de-agglomeration principle highly effective. By definition, the obtained fine particle fraction with this type of principle is highly flow rate dependent.

For the concept disclosed in DE 19522416, the angle of impact against residual sections of the inner wall of the circulation chamber is 45 degrees, which is optimal in the balance between angle of impact and residual particle velocity, but the distance between the sections is quite short. In addition to that, the number of air bypass channels to the circulation chamber is high, which reduces the air velocity inside these channels. Therefore, the acceleration of the carrier particles in the new direction after collision is not maximal. The concept is highly appropriate for the disintegration of soft spherical pellets, as described previously, but for adhesive mixtures, best possible result can not be obtained.

For the newly developed concept for adhesive mixtures described hereafter (technical description), the basic shape of the circulation chamber is an octagon with eight angles of 45 degrees each. However, in contrast with DE 19522416, not all sides of the octagon have the same length: four longer sides are alternated with four shorter sides. The latter comprise the impaction sites for the carrier particles. Also in contrast with this previously described concept, the number of bypass channels is only three. Therefore, the air velocity inside these channels is much higher at the same inspiratory flow rate through the circulation chamber. Accordingly, the drag force for the acceleration of the carrier particles inside the chamber is much higher. Particles are accelerated along the longest sides of the octagon and impact on the adjacent shorter side. The higher initial drag force and the longer trajectories for particle acceleration both contribute to a higher impact velocity.

On average, particles bounce off the impact side with approximately the same angle as the angle of impact and after deflection, they are immediately accelerated towards the next impact side. However, some scattering of particles occurs in other directions, due to the irregular shape of carrier crystals. As a result of this scattering at higher velocity (compared to the carrier particle impact velocity at the same flow rate in the concept described in DE 19522416), the rate of passage through the discharge channel is higher. Although this rate of discharge can be controlled quite well by selecting the appropriate carrier size distribution and diameter for the discharge channel, as has been discussed previously. The highest carrier circulation velocity (of all concepts) in PCT/NL01/00133, does not result in the highest carrier discharge rate from this basic air classifier concept, because of the obtuse angle of impacting and the extension of the discharge tube projecting into the circulation chamber. Most particles in this concept are not scattered in the direction of the discharge channel, and the few ones that are, are (with a few exceptions) unable to enter this channel because of its extension protruding from the top wall of the classifier.

The average particle velocity with which particles circulate inside the newly developed concept is between those of the concepts disclosed in DE 19522416 and PCT/NL01/00133 at the same inspiratory flow rate. The reason for this is, that the distance between the impact sites in this new concept is shorter than the distance required to accelerate the particles towards the air velocity inside the chamber. This has the advantage that the fine particle fraction (FPF) is less dependent on the inspiratory flow rate than that of PCT/NL01/00133.

As for the concept with near-complete carrier retainment (PCT/NL01/00133), the FPF is dependent on the residence time in the circulation chamber of the newly developed concept for adhesive mixtures too. This is shown in FIG. 8 for two different designs of this new concept (open and closed symbols) in comparison with the FPF from the de-agglomeration means described in DE 19522416 (asterisks), using a mixture with Capsulac 60 and 2% budesonide. The closed symbols represent the FPF's from the most efficient design of this concept. The increased efficiency has reduced the necessary circulation time for the detachment of approximately 40% of the drug particles from the carrier crystals from two to less than one second.

The figure shows the same type of correlation between residence time and FPF as that in FIG. 3B, but there are some relevant differences. For the basic air classifier in FIG. 3B, no sheath flow was used. Consequently, the whole inspiratory air flow was conducted through the de-agglomeration chamber during the experiments. For the newly developed concept for adhesive mixtures with controlled carrier passage in FIG. 8, about ⅓ of the total flow rate has been used as sheath flow in order to confine the air flow resistance of the concept to an agreeable value for the patient. The curves in FIG. 3B represent the percentages of drug that have been detached from the carrier crystals, whereas the curves in FIG. 8 are for the collected fine particle fraction in a cascade impactor. Therefore, the difference between both types of curves is the drug adhesion in the inhaler device and the inlet tube to the impactor. There may also be some losses of the finest drug particle fractions from passage through the final impactor stage. Finally, the residence time in FIG. 3B is for the near-complete carrier fraction, whereas the residence time in FIG. 8 is the time necessary for complete carrier discharge. Average duration of carrier circulation in the newly developed concept is therefore approximately half the residence time as presented.

Taking all these differences in account, it can be concluded from comparison of FIGS. 3B and 8, that the difference in efficiency between the newly developed concept and the concept presented in PCT/NL01/00133 is quite substantial. The obtained fine particle fraction for the optimized concept in FIG. 8 is nearly 45% of the dose after a residence time of 1 second, meaning that average circulation time was only approximately 0.5 s. This is about the same percentage as found for the drug particle detachment in FIG. 3B after 0.5 s. So, after correction for (a) the losses in FPF due to adhesion in the inhaler and inlet tube and (b) the difference in flow rate through the de-agglomeration chamber (reduced by one third for the newly developed concept as a result of the application of sheath flow), the drug detachment within half a second is much higher in this new concept. By reducing the sheath flow, a further efficiency increase is possible, but the resulting increase in resistance to air flow might make use of the inhaler less agreeable for the patient.

Reducing the residence time to a period of less than 1 to 1.5 seconds, or even shorter for flow rates higher than 60 l/min, seems more or less mandatory considering the recent regulatory directives, which demand that the complete dose can be inhaled within 2 liters.

As shown in FIG. 8, this practically confines the fine particle fraction to approximately 40 to 50% of the nominal dose for adhesive mixtures, even when they are inhaled from a highly efficient disintegration means. Especially for the range up to one second, FPF strongly decreases with decreasing circulation time. So, a very careful tuning of the residence time is necessary to obtain the best possible therapeutic effect from an inhalation dose. Within the same range of circulation times (0 to 1 s), the properties of the carrier material in adhesive mixtures, that are relevant to drug particle detachment, are most critical, too. Therefore, good powder de-agglomeration up to one second residence time is difficult to achieve, and this should be a serious argument for reconsideration of the previously mentioned demand.

DESCRIPTION OF PREFERRED EMBODIMENTS OF THE INVENTION

The present application includes discussion of DE 19522416 and PCT/NL01/00133 and both of these documents are hereby incorporated by reference.

The modular design of the de-agglomeration means is another aspect of the invention. It enables exchange of different concepts (e.g., basic air classifier substituted by the optimized de-agglomeration principle for adhesive mixtures) within the same inhaler device and/or the use of the concepts in different inhaler. The choice of concept depends on (a) specific application or (b) type of formulation.

Additional to the modular design with different concepts for the de-agglomeration chamber, various embodiments and variations are useful and preferred, and include the use of longitudinal flow baffles inside the discharge channel of the circulation chamber that eliminate the tangential flow component (at the cost of increased drug accumulation inside this channel); and the use of a special mouthpiece for the entrapment of large carrier particles that are flung in radial direction by centrifugal action immediately after discharge from the mouthpiece. This reduces irritant mouth feel and candidiasis from carrier deposition in the mouth. The mouthpiece can be designed as a double (co-axial) cylinder, in such a way that an annular chamber is created between both cylinders for storage of the retained carrier particles. Before inhalation, the outer mouthpiece is displaced against the inner cylinder (by rotation, using a screw thread, or by pulling) in longitudinal direction in order to create a passageway for the carrier particles. After inhalation, the annular chamber is closed again.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 10B:
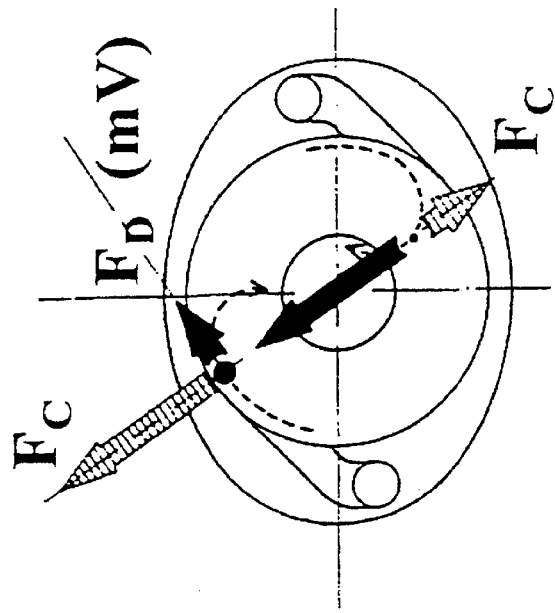
Figure 10A:
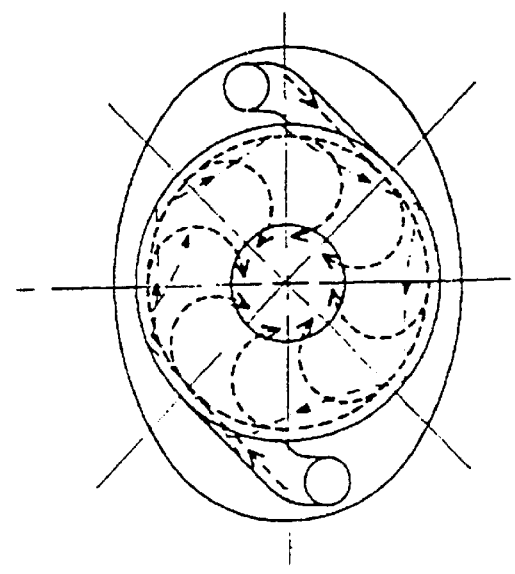

FIG. 2 is a diagram showing cut-off diameter of an air classifier similar to the concept disclosed in PCT/NL01/00133 as function of the flow rate through the classifier for colistin sulfate with a relatively wide size distribution between 0.7 and 87 μm as measured with a laser diffraction apparatus (Sympatec, HELOS compact, model KA with 100 mm lens) after RODOS dispersion. The cut-off values equal the $X_{100}$-values from laser diffraction analysis of the aerosol cloud from the test inhaler connected to a special inhaler adapter (RuG's test model);

FIG. 3A is a diagram showing carrier residue, extrapolated to 100% withdrawal, for adhesive mixtures with 0.4% budesonide as function of the inhalation time at 60 l/min for an air classifier similar to the concept disclosed in PCT/NL01/00133. The continuous lines with open symbols represent the mixtures after 10 minutes mixing time; the closed symbols with interrupted lines are for mixtures after 120 minutes mixing time. Carrier materials are sieve fractions 45–63 μm and 150–200 μm derived from Pharmatose 150M and size fraction 150–200 pm from Capsulac 60. Dose weight is 25 mg;

FIG. 3B is a diagram showing drug release rate for mixtures with 0.4% budesonide at 60 l/min for an air classifier similar to the concept disclosed in PCT/NL01/00133. The curves have been calculated as 100 minus the values in FIG. 3A;

FIG. 4 is a diagram showing fine particle fractions for some marketed dpi's and two different concepts of the invention, all with adhesive mixtures, obtained a 4 kPa across the inhalers. Glaxo Diskus and Diskhaler both with Flixotide and Serevent formulations; ISF inhaler with budesonide (Cyclocaps,Pharbita) and Foradil (Ciba Geigy). Air classifier CII, similar to the conception PCT/NL01/00133, with 0.4% budesonide mixtures for the indicated Pharmatose carriers; Novolizer (with the concept of DE 19522416) with mixtures of 1% budesonide resp. 1% salbutamol on Capsulac 60 (left beams per drug) and a mixture of Capsulac 60 and 5% Pharmatose 450M (right beams per drug);

FIG. 5 is a diagram showing residence times of narrow sieve fractions derived from Pharmatose 110M as function of mean fraction diameter at three different flow rates in the newly developed concept for adhesive mixtures with 8 mm discharge channel. Dose weight, is 10 to 11 mg;

FIG. 6 is a diagram showing residence times of different types of carrier material in the newly developed concept for adhesive mixtures, for two different discharge channels at 60 l/min. Closed symbols are narrow sieve fractions derived from Pharmatose 110M; open symbols are for marketed lactose products with different median diameters. Dose weight is approximately 11 mg;

FIGS. 7A and 7B are diagrams showing residence times of adhesive mixtures with two different drug loads (0.4 and 4.0% budesonide), in comparison with the unmixed carrier materials, for the newly developed concept with 7 (FIG. 7A), respectively 8 mm (FIG. 713) discharge channel at 60 l/min. Dose weight is approximately 14 mg. Carrier fractions have been derived from Pharmatose 110M (63–100 and 150–200 μm) and Capsulac 60 (150–200 μm);

FIG. 8 is a diagram showing fine particle fraction as function of residence time indifferent concepts of the newly developed de-agglomeration principles for adhesive mixtures measured with a four stage Lenz Labor impactor of the Fisons type at approximately 4 kPa across the devices. Mixture: Capsulac 60 with 2% budesonide. Residence times for FIGS. 5, 6, 7 and 8 have been obtained from dP-suppression measurement;

FIG. 9A is an exploded perspective view of the basic air classifier concept of the disintegration means with carrier retainment;

FIGS. 9B and 9C are a plan views of the inhaler body of FIG. 9A;

FIG. 9D is a cross-sectional view of the assembled basic air classifier concept of FIG. 9A;

FIGS. 10A and 10B are diagrams which show the main flow components of the stream lines of the air and particle trajectories inside the circulation chamber of the basic air classifier in relation to the forces acting on these particles;

FIG. 11A is an exploded perspective view of the concept with air barrier inside the circulation chamber which prevents substantial fine particle adhesion onto the interior chamber wall, especially during break-up of soft spherical pellets;

FIG. 11B is a plan view of the inhaler body shown in FIG. 11A;

FIG. 12A is an exploded view of the concept with separate acceleration sides and impact sides and a controlled release rate for the carrier crystals;

FIG. 12B is a plan view of the inhaler body shown in FIG. 12A; and

FIGS. 13A, 13B1, 13B2, 13B3, 13B4, 13C, 13D and 13E are exploded views of some different modifications of the top plate of the circulation chamber with discharge channel connected thereto, for the concepts shown in FIGS. 11 and 12.

The hereabove outlined invention and all its specific features, as partly elucidated in the FIGS. 1 to 8, will become apparent from the technical description given hereafter, which is to be read in connection with FIGS. 9 to 13.

Although the exemplification set out herein illustrates embodiments of the invention, in several forms, the embodiments disclosed are not intended to be exhaustive or to be construed as limiting the scope of the invention to the precise forms disclosed.

It will be understood by a person skilled in the art that the FIGS. 9 to 13 show possible embodiments by way of example and that these can be modified in many different ways without departing from the scope of the invention as discussed in the outline and further defined in the claims.

Throughout the drawings, the same or like elements are designated with the same reference sign to ease understanding of the invention.

DETAILED DESCRIPTION OF THE INVENTION

FIG. 9 shows the basic air classifier connected to an inhaler body 1 without depicting details of the dose mechanism from which the powder quantity, representing a single dose, is entrained by part of the inspiratory air flow through the powder channel 2. The circulation chamber 3 of the air classifier is cylindrical with a height being smaller than its diameter and a minor rounding 4 at the position of the transition from the cylindrical wall 5 to the bottom wall 6 of the chamber 3. The particle laden air through the powder channel 2 is forced to change its flow direction after reaching the top plate 8 of the circulation chamber 3 by a 90 degrees turn into the final section 2A of the powder channel 2, which approaches the circulation chamber as a tangent to its cylindrical wall 5. On the opposite side of the circulation chamber 3 is the entrance for the bypass flow to this chamber, being a second part of the inspiratory flow, which is the final section 9A of a bypass flow channel 9. This final section 9A of the bypass flow channel 9 is also constructed as a tangent to the cylindrical wall 5 of the circulation chamber 3 in order to support the basically circular air flow inside this chamber 3, as shown in FIG. 10. The depths of the final sections 2A and 9A of the powder flow channel 2 and bypass channel 9, which have rectangular cross sections, are approximately half the depth of the circulation chamber 3 of the classifier. The bypass flow channel 9 upstream of its final section 9A has been created by reducing the thickness of the outer cylindrical wall section 10A of the circulation chamber 3, adjacent to the channel section 9A, to the same diameter as that for thinner section 10B and over the same height as the depth of the final section of the bypass flow channel 9A.

The cylindrical wall 10 of the circulation chamber 3 has two thinner sections 10B and two thicker sections 10A through which the air passageways 2 and 9 have been constructed, all four sections extending over equal parts of the circumference of this wall, corresponding to angles of about 90 degrees. In the top plate 7 of the central inhaler housing 1, at the positions corresponding with the thinner sections of wall 10, there are openings 11 that serve as passageways for the partial bypass flow and sheath flow. Air coming through these passageways 11 enters an annular chamber 12, as shown in FIG. 9D, between the tubular mouthpiece cylinder 13 and the cylindrical wall 10 of the circulation chamber 3. As a result of the local differences in thickness for the cylindrical wall 10 of the circulation chamber 3, the annular chamber 12 has different widths. FIGS. 9A to 9D do not show the inlet opening for the inspiratory, flow and the splitting up of this flow into (a) a partial flow traversing the dose measuring or dose supplying section of the inhaler before entering the circulation chamber through the powder channel 2, and (b) another partial flow entering the annular chamber 12 through the openings 11. These aspects are part of the inhaler design and not relevant to the invention.

Figure 9A:
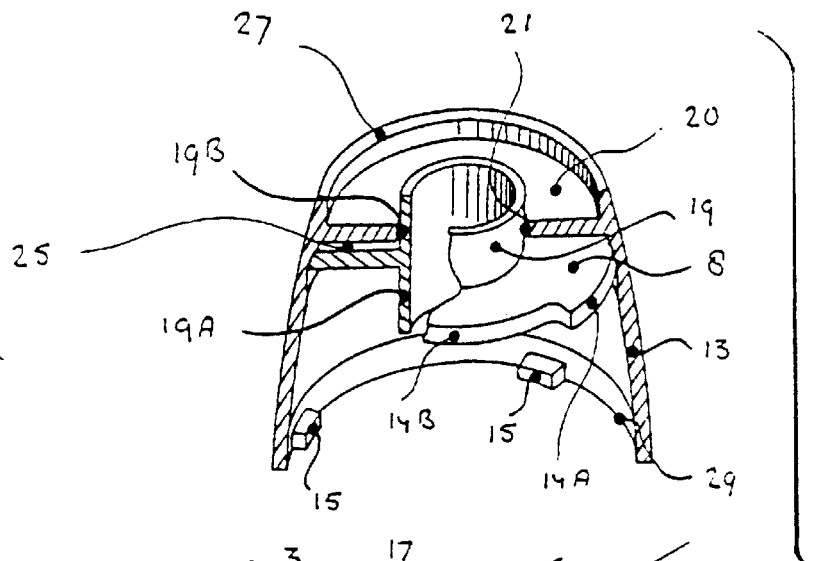
Figure 9B:
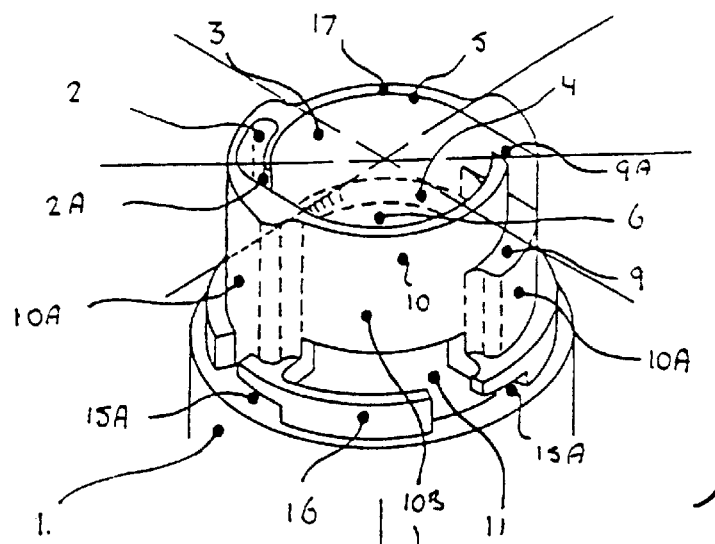
Figure 9B:
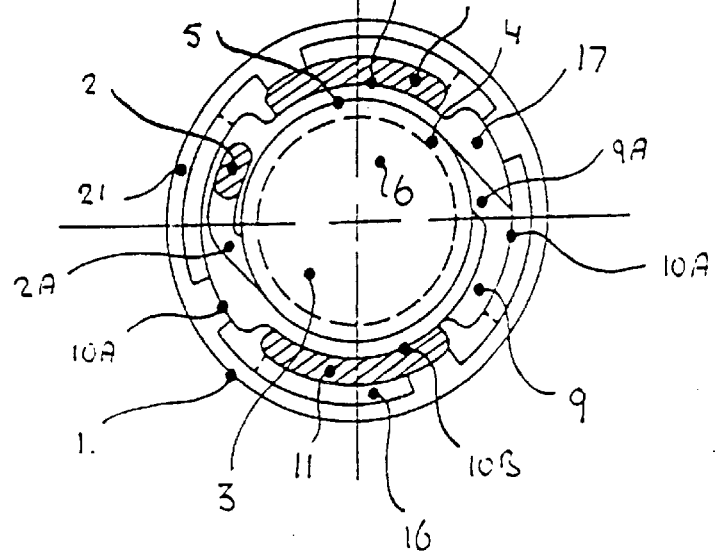
Figures 9C, 9D:
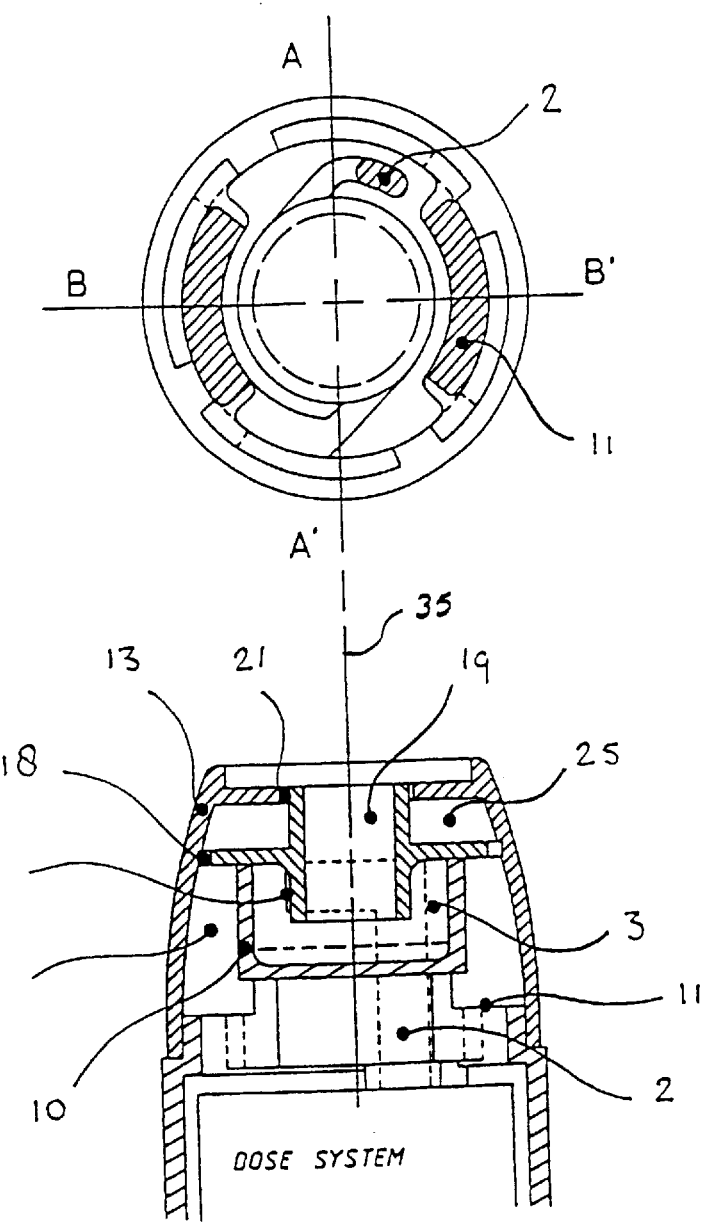

In FIG. 9A, the top plate 8 of the circulation chamber 3 is a separate part which is press fitted to the mouthpiece cylinder 13 by a mild jamming into this cylinder. The mouthpiece cylinder 13 is positioned over the cylindrical wall 10 of the circulation chamber 3 and fixed to the inhaler housing 1 by a bayonet catch of which the projections 15, connected to the mouthpiece cylinder 13, fit in the slightly tapered gaps 15A underneath the locally interrupted raised border 16 adjacent to the exterior wall 10 of the circulation chamber 3. In the end position of the projections 15 in the tapered slits 15A, the top plate 8 is pressed firmly against the rim 17 of the cylindrical wall 10 of the circulation chamber 3. FIG. 13E shows that this top plate 8 can also be an integral part of the circulation chamber 3; alternatively (not shown), it can be an integral part of the mouthpiece cylinder 13 itself. The top plate 8 as shown in FIGS. 9 and 9A, is basically circular but has two different diameters 14A and 14B for different sections of this plate, corresponding with the different diameters 10A and 10B for the cylindrical wall 10 of the circulation chamber 3 when the mouthpiece cylinder 13 is snapped into position. The space 18 in FIG. 9D between the interior wall of the mouthpiece cylinder 13 and the top plate 8 of the circulation chamber 3, at the positions where the top plate has a reduced diameter, serves as a passageway for the sheath flow, which is a third part of the total inspiratory flow. The total cross sectional area of the two quarters of the basically annular slit between the interior wall of the mouthpiece channel 13 and the top plate 8 of the circulation chamber contributes to the air flow resistance of the total passageway for the sheath flow.

The top plate 8 of the circulation chamber 3 has a tubular passageway 19 for release of the aerosol cloud from said chamber 3. The discharge channel 19 shares its axis with the circulation chamber 3 but has a smaller diameter than the chamber 3. A lower part 19A of the channel 19 is projecting into the circulation chamber 3 over a distance being slightly longer than half the depth of the chamber 3. The other part 19B of the channel 19 protrudes through a top plate 20 of the mouthpiece cylinder 13. The outer diameter of the discharge channel 19 is slightly smaller than the diameter of the circular hole 28 (FIG. 11) in the top plate 20, thus, to create a narrow annular passageway 21 for the sheath flow. This narrow passageway 21 also contributes to the total air flow resistance for the sheath flow. Mentioned resistances for the sheath flow are carefully balanced in relation to the air flow resistance of the circulation chamber 3 in order to control the partial flow rates through the inhaler. The annular slit 21 between the discharge channel 19 and the top plate 20 of the mouthpiece cylinder 13 has no interruptions, in order to create an unbroken co-axial sheath of particle free air around the aerosol cloud from the discharge channel 19.

The working principle of the basic air classifier concept is explained in FIG. 10. FIG. 10A shows relevant components of the stream lines of the air inside this chamber, whereas FIG. 10B is a schematically representation of the forces acting on particles of different sizes and in different circulation regions. The main component of the stream lines along the periphery of the circulation chamber 3 in FIG. 10A is in tangential direction, whereas closer to the discharge channel 19, which starts from the center of the chamber 3, flow components in radial and longitudinal directions increase as the air enters this channel. Agglomerates with relative large inertia, entering the circulation chamber 3 along its periphery, start a basically circular trajectory along its inner wall 5 where the centrifugal force (Fc) is dominant (FIG. 10B). Even after collision with the inner wall 5 of the circulation chamber 3, as a consequence of which particles may bounce off this wall and approach the discharge channel 19 at the center of this chamber 3, most large agglomerates will return to the original circular pathway by their high momentum (mV), along which they are accelerated by the drag force (FD). However, fine particles that are detached from these agglomerates, have a much lower momentum, whereas the drag force is relatively high compared to the centrifugal force, especially in circulation regions at a certain distance from the wall 5 of the circulation chamber 3. These particles are able to follow the streamlines of the air and are discharged from the circulation chamber 3, whereas the larger agglomerates are retained inside this chamber 3 by the action of the centrifugal force.

The basic air classifier is particularly suitable for the disintegration of adhesive mixtures, in which the large carrier crystals act as sweeper crystals keeping the interior cylindrical wall 5 of the circulation chamber 3 free from adhering fine drug particles. Without the presence of these sweeper crystals, fine particle accumulation inside this chamber 3 is substantial, as in similar swirl, whirl or cyclone chambers applied in other dry powder inhalers.

In another embodiment of the invention, as shown in FIG. 11, the principle is particularly suitable for the disintegration of soft spherical pellets or adhesive mixtures for which larger particles, such as carrier crystals, are not retained but gradually released from the circulation chamber 3. This concept is different from the concept in FIG. 9 with respect to the shape and depth of the circulation chamber 3, the number and shape of the channels for the bypass flow 9, the shape of the powder channel 2, the top plate 8 of the circulation chamber and the discharge channel 19 for the circulation chamber connected thereto, as well as the air passageway towards the bypass channels 9. In addition to that, some constructional differences between the concepts in the FIGS. 9 and 11 are shown that are not essential for the scope of the invention.

Figure 11A:
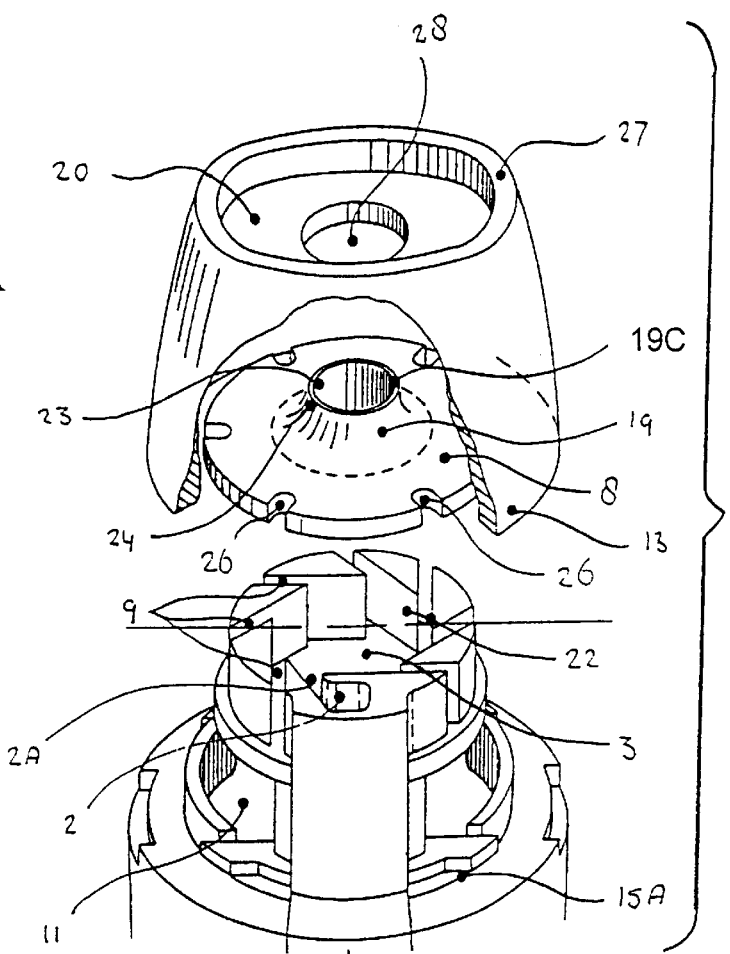
Figure 11B:
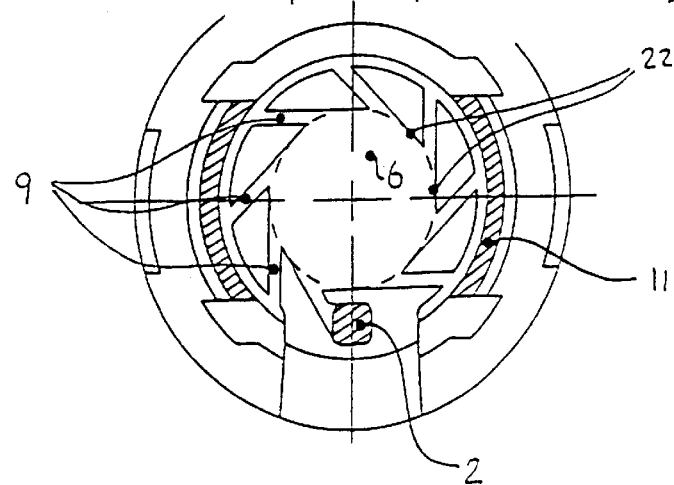

The concept in FIG. 11 has seven identical channels 9 for the bypass flow, of which each has a generally rectangular shape in cross section and about the same depth as the circulation chamber. The channels 9 provide the circulation chamber 3 in top view largely with the shape of an octagon with eight identical open angles of 135 degrees between the remaining sections 22 of the interior wall 5 of the circulation chamber 3. The powder flow channel 2 is the same as that for the concept in FIG. 9, except for the depth of the final section 2A of the channel 9 which is the same as that for the circulation chamber 3. Air flows from the bypass 9 and powder 2 channels skim over these remaining sections 22, which are the impact zones for the larger agglomerates. Only larger particles are able to traverse these flows as the result of their high momentum. Fine particles with much lower inertia, are turned off course by the bypass flows, which create a so-called internal air barrier between these particles and the remaining wall sections 22. Consequently, fine particles are unable to hit these sections 22. Therefore, the fine particle adhesion onto the impact zones of sections 22 is extremely low, compared to the adhesion onto the interior wall 5 of the circulation chamber 3 for the concept shown in FIG. 9, even from the disintegration of spherical pellets. The circulation chamber 3 of this concept does not have a rounding between the remaining sections 22 of its interior wall and its bottom 6.

The discharge channel 19 in the center of the top plate 8 for the circulation chamber 3 for the concept in FIG. 11 does not have a projection into this circulation chamber 3. The channel 19 has an inner wall 23 with a constant diameter, but an outer wall 24 with an exponentially increasing diameter from the top rim 19C towards the top plate 8 of the circulation chamber 3. This is to direct the sheath flow through the annular channel 21 between the discharge channel 19 and the top plate 20 of the mouthpiece cylinder 13 from the cavity 25 (as depicted in FIG. 9) between both top plates 20 and 8 as smoothly as possible. Because of the absence of a protruding part 19A of the discharge channel 19 from the top plate 8 of the circulation chamber 3 into this chamber 3, the passageway into the discharge channel 19 for larger particles that bounce off the remaining sections 22 of the cylindrical wall of the circulation chamber 3 after impact, is much wider. This increases the zone from which large particles can enter the discharge channel 19. In addition to that, the angles with which particles bounce off the impact zones 22 are less obtuse than those in the basic air classifier with a circular inner wall 5 (concept in FIG. 9). As a consequence, the particle trajectories inside the circulation chamber 3 of the concept in FIG. 11 more frequently traverse the zone from which the particles can enter the discharge channel 19. Hence, large particles are gradually released from the circulation chamber 3 and there is no carrier retainment for this particular concept of the disintegration principle.

The top plate 8 of the circulation chamber 3 for the concept in FIG. 11 has the same diameter for its entire circumference. The supply of sheath flow from annular chamber 12 (FIG. 9A) to cavity 25 (FIG. 9) between this top plate 3 and the top plate of the mouthpiece cylinder 13 is through a number of nicks 26 along the circumference 14 of the top plate 8, which have carefully controlled shape and dimensions. For the concept in FIG. 11, the number of nicks 26 is six and they are symmetrically distributed over the circumference 14 of the top plate 8 with angles of 60 degrees between them. The total air flow resistance of these nicks 26 in conjunction with the air flow resistance of the annular channel 21 between the discharge channel 19 and top plate 20 of the mouthpiece cylinder 13 determines the rate of sheath flow in relation to the partial bypass and powder flow rate through the inhaler.

Figure 1:
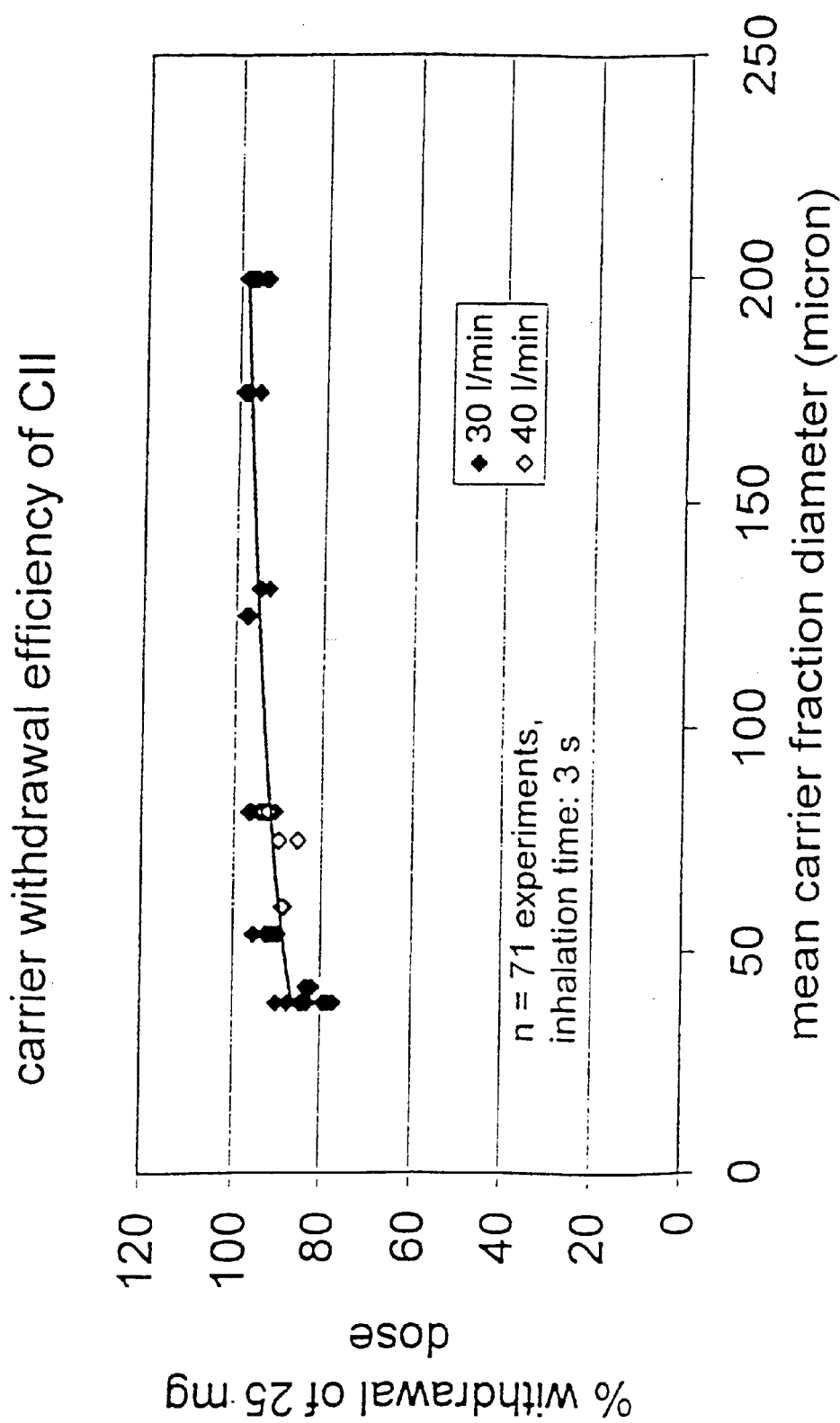
FIG. 1 is a diagram showing carrier withdrawal efficiency of an air classifier similar to the concept disclosed in PCT/NL01/00133 as function of mean carrier diameter for narrow size fractions of different types of crystalline alpha lactose monohydrate at 30 and 40 l/min. Dose weight is 25 mg.
Figure 2:
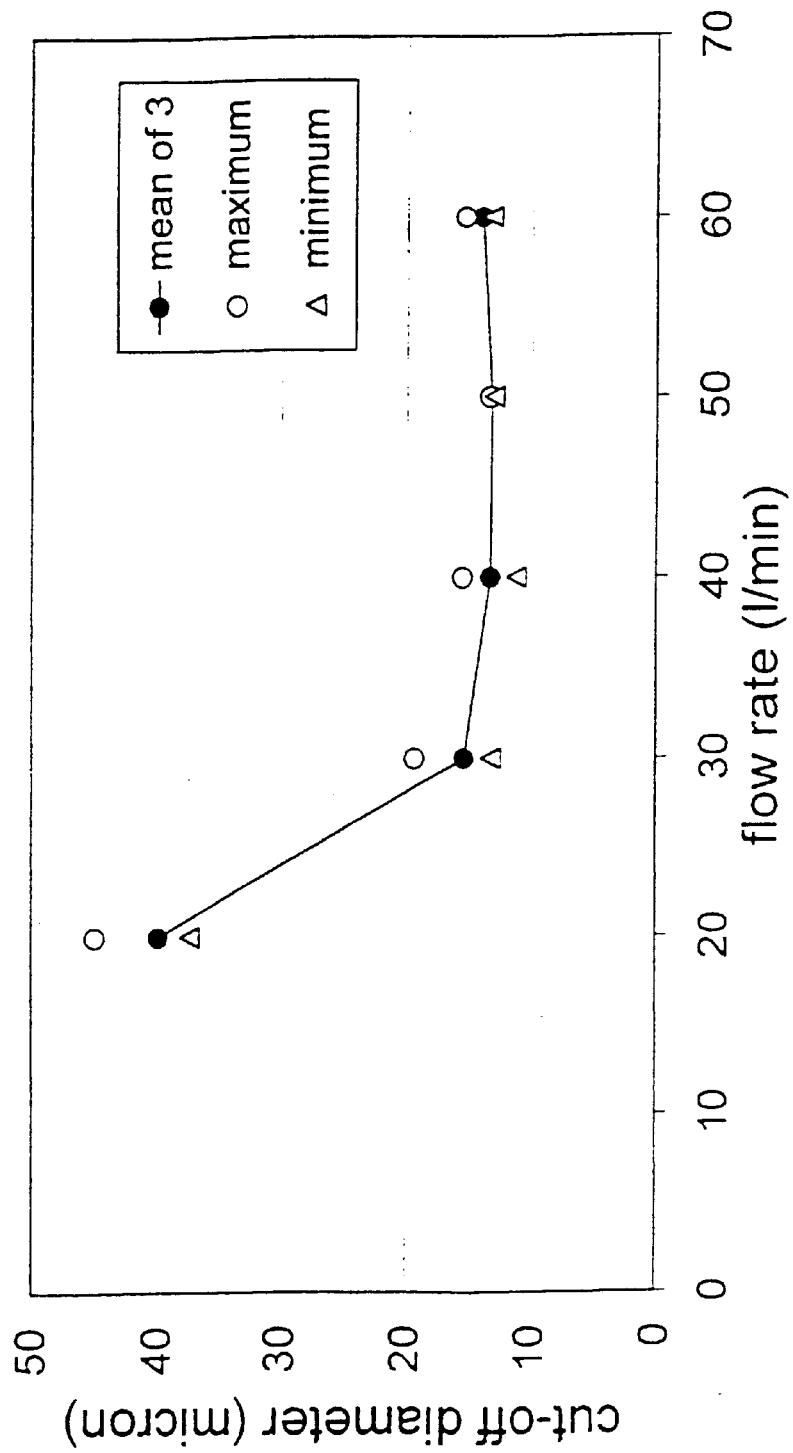
Figure 3A:
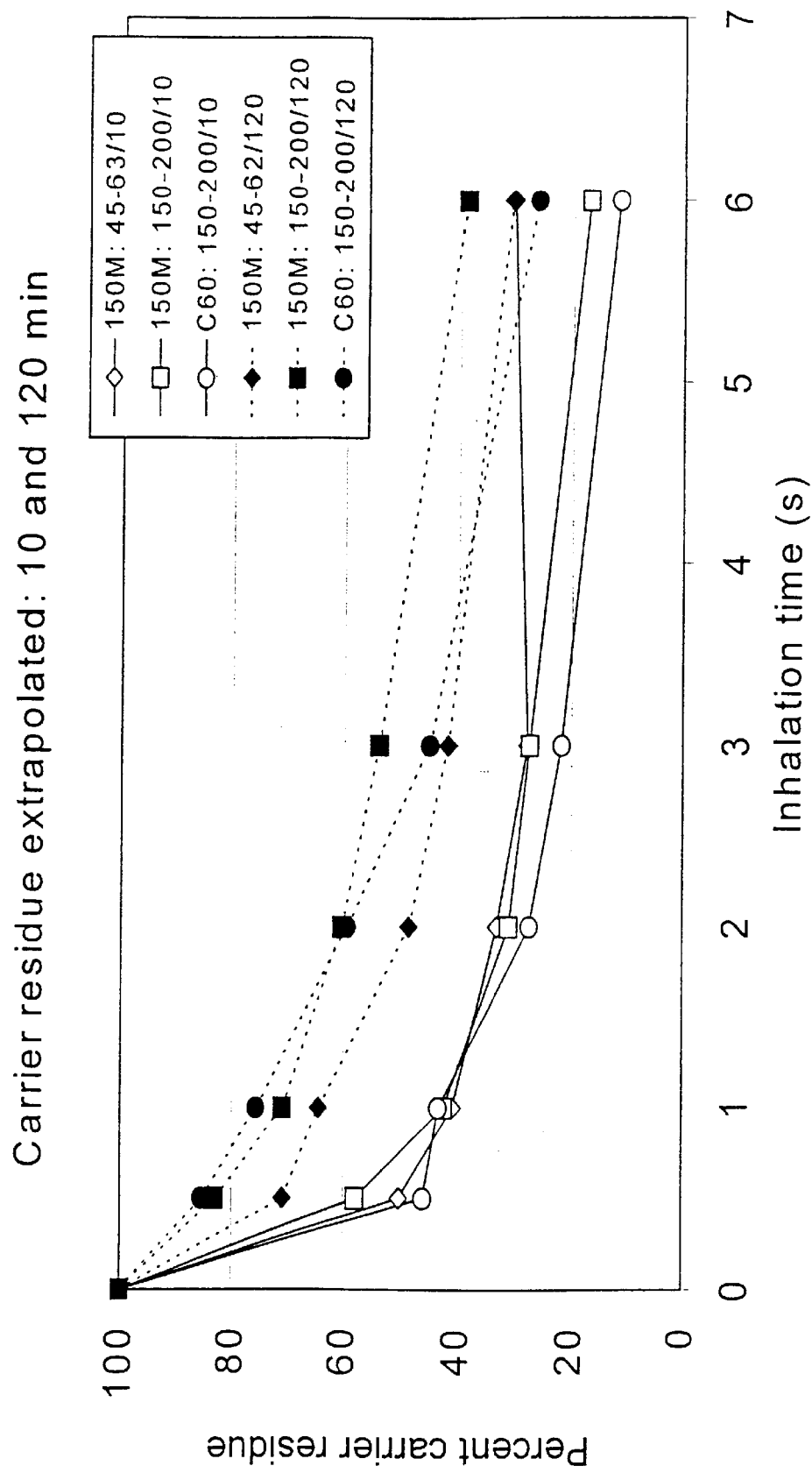
Figure 3B:
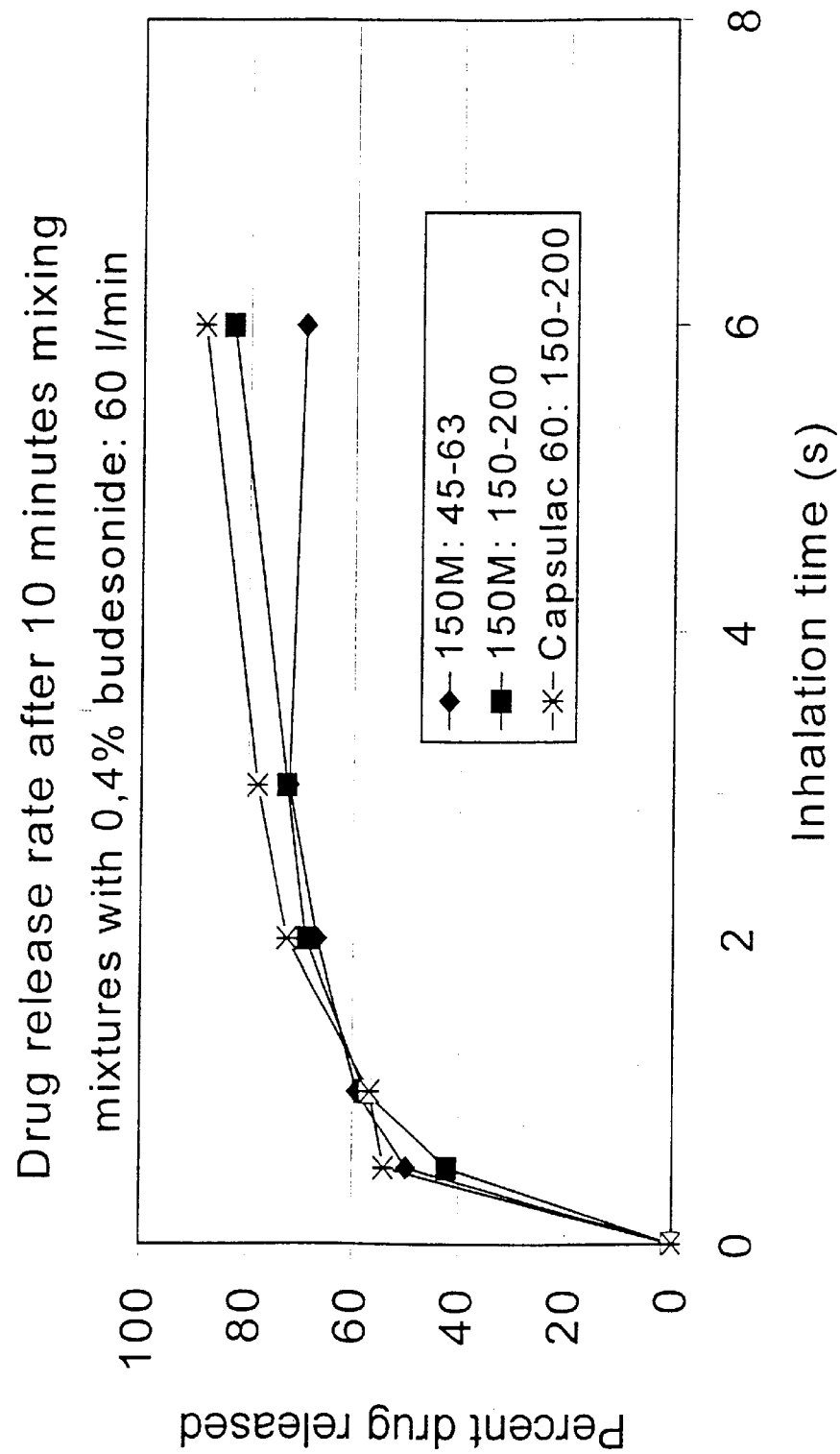

Not particularly relevant to the scope of the invention is the shape of the mouthpiece cylinder 13, which is circular with a gradually decreasing diameter from bottom rim 29 to top rim 27 for the concept in FIG. 9, but rather changing from circular to oval in the same direction for the concept depicted in FIG. 1. The upper rim 27 may be raised relative to the top plate 20 of the mouthpiece cylinder 13.

Figure 4:
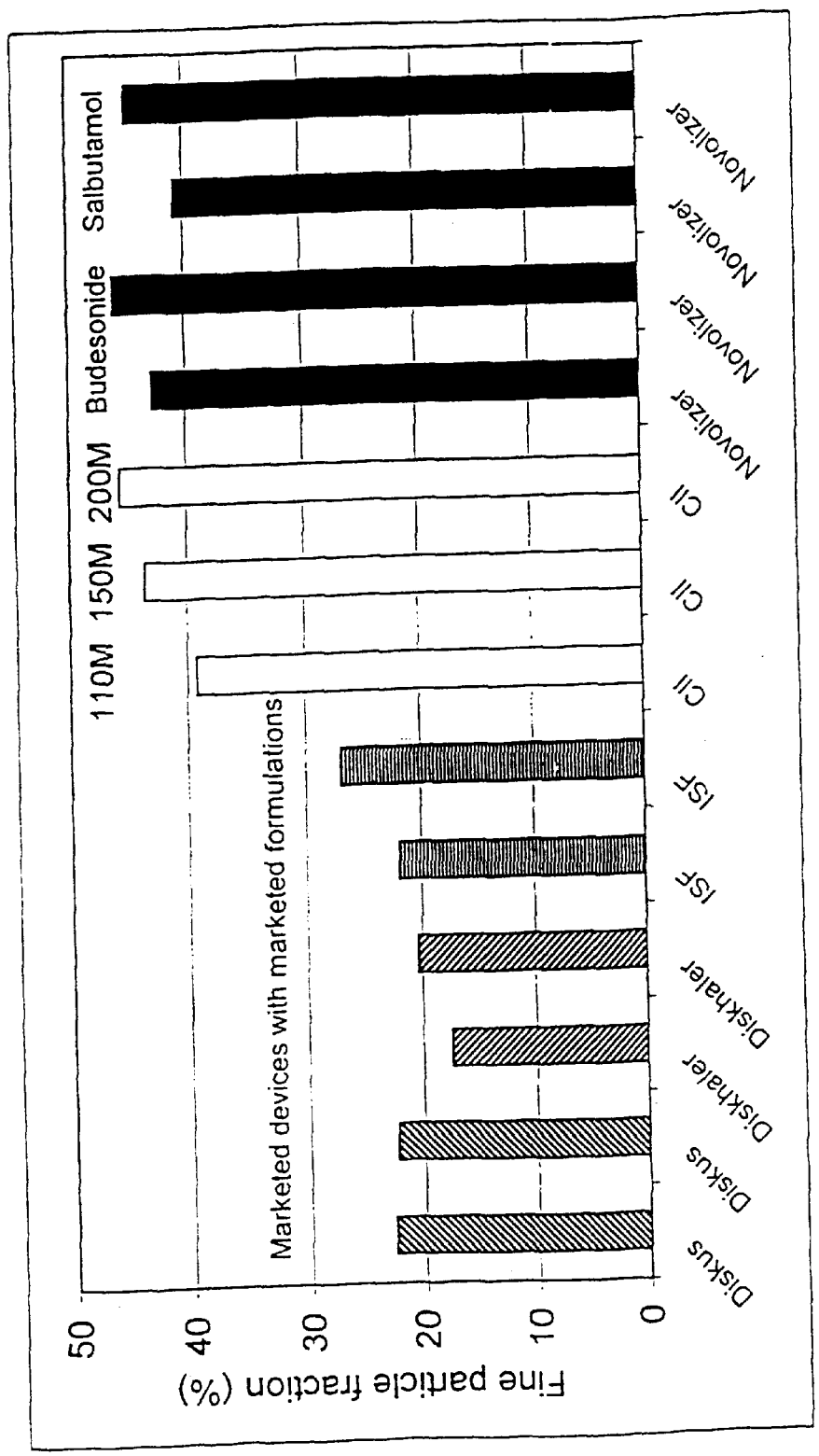
Figure 5:
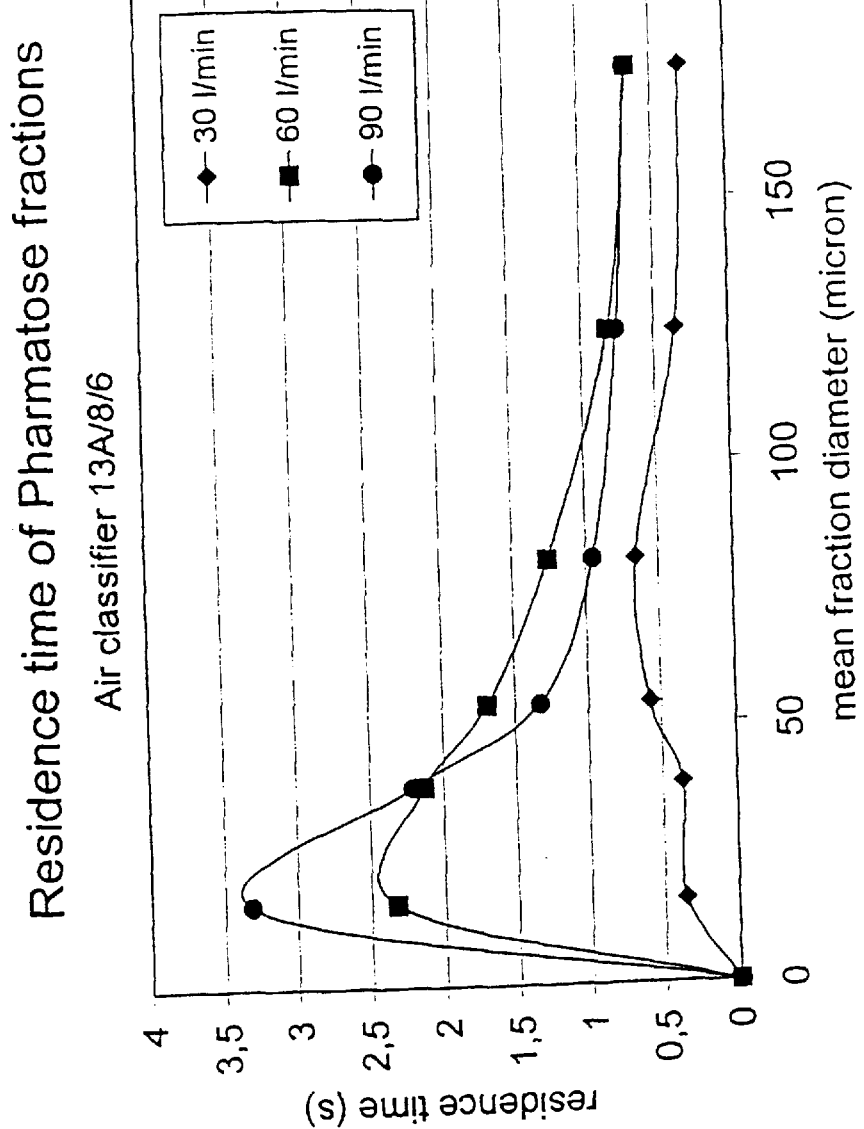
Figure 6:
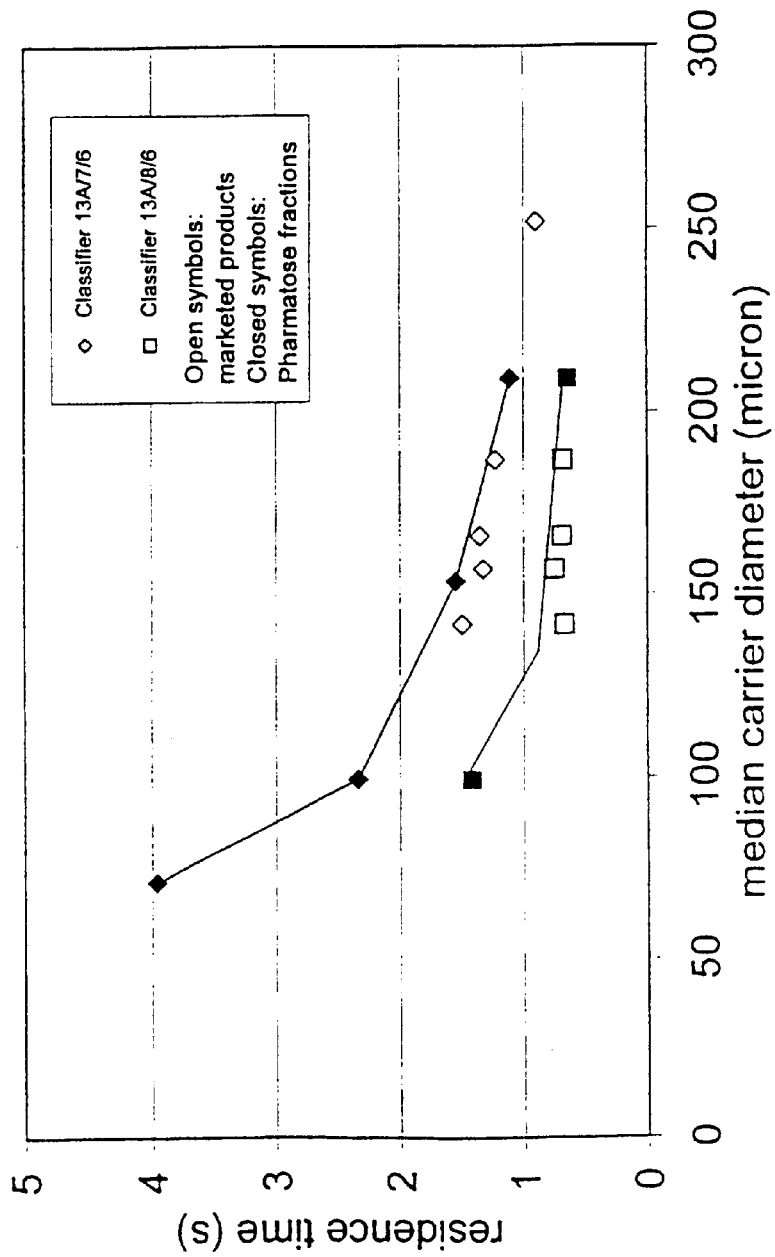
Figure 7A:
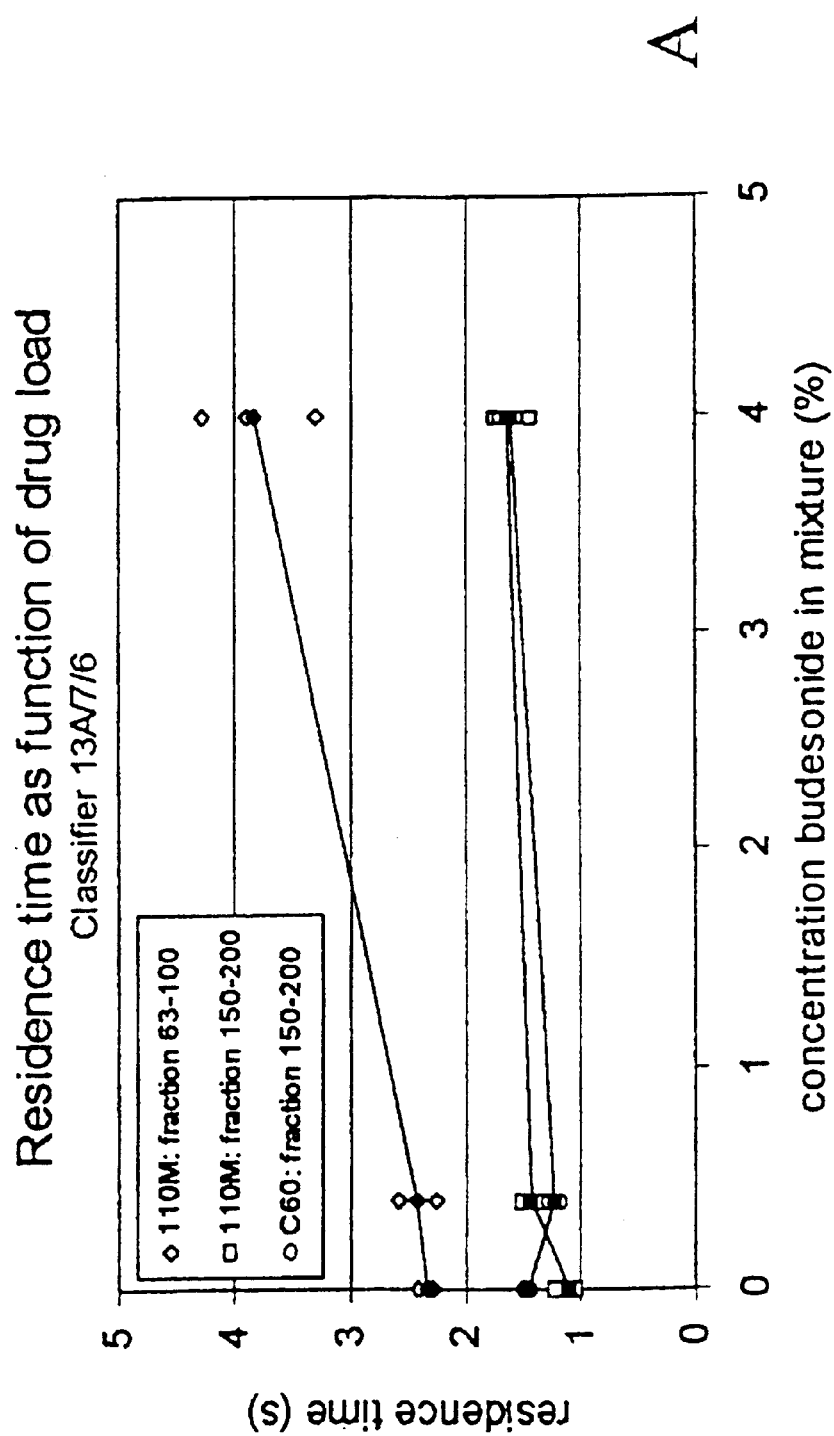
Figure 7B:
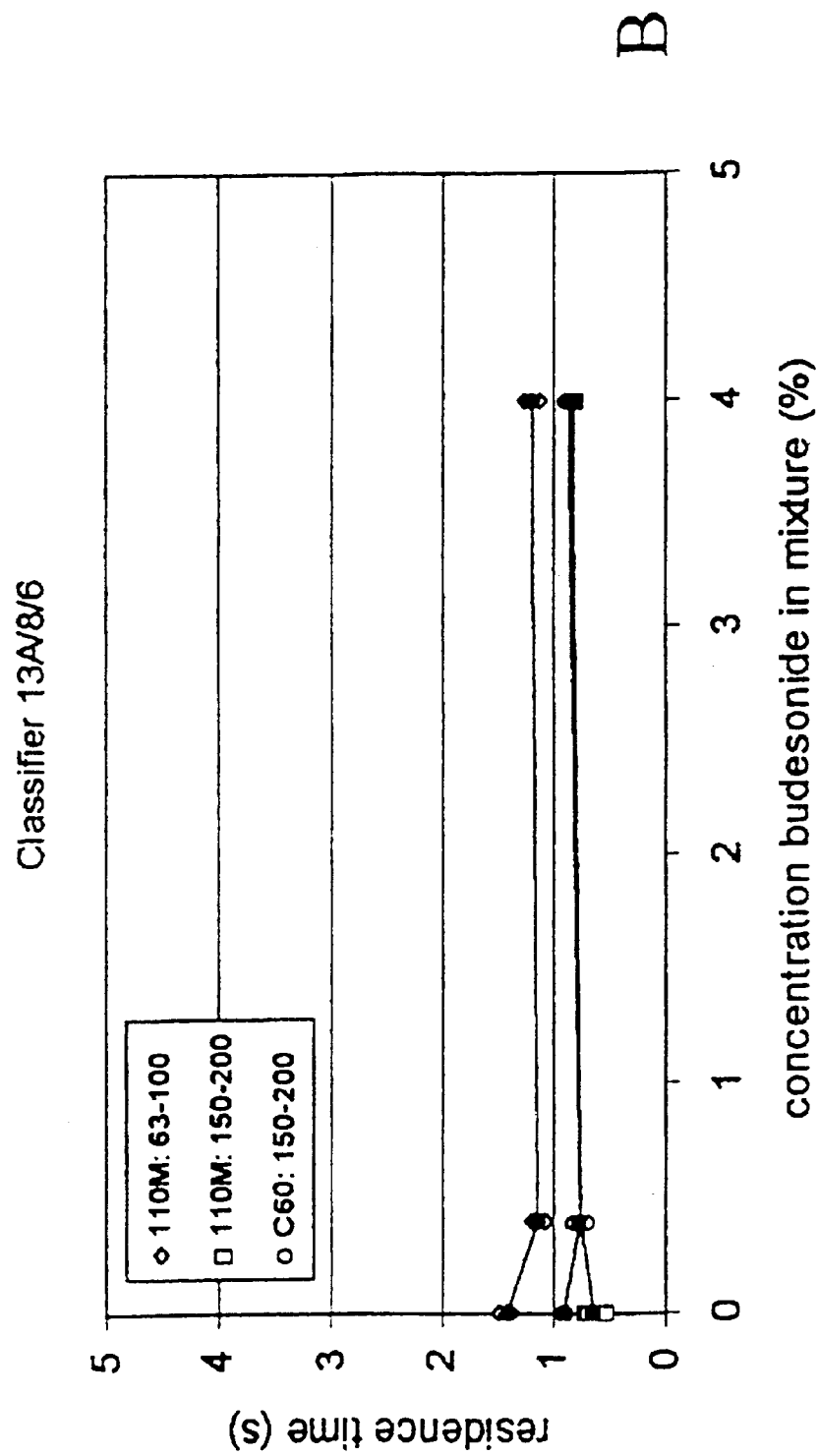
Figure 8:
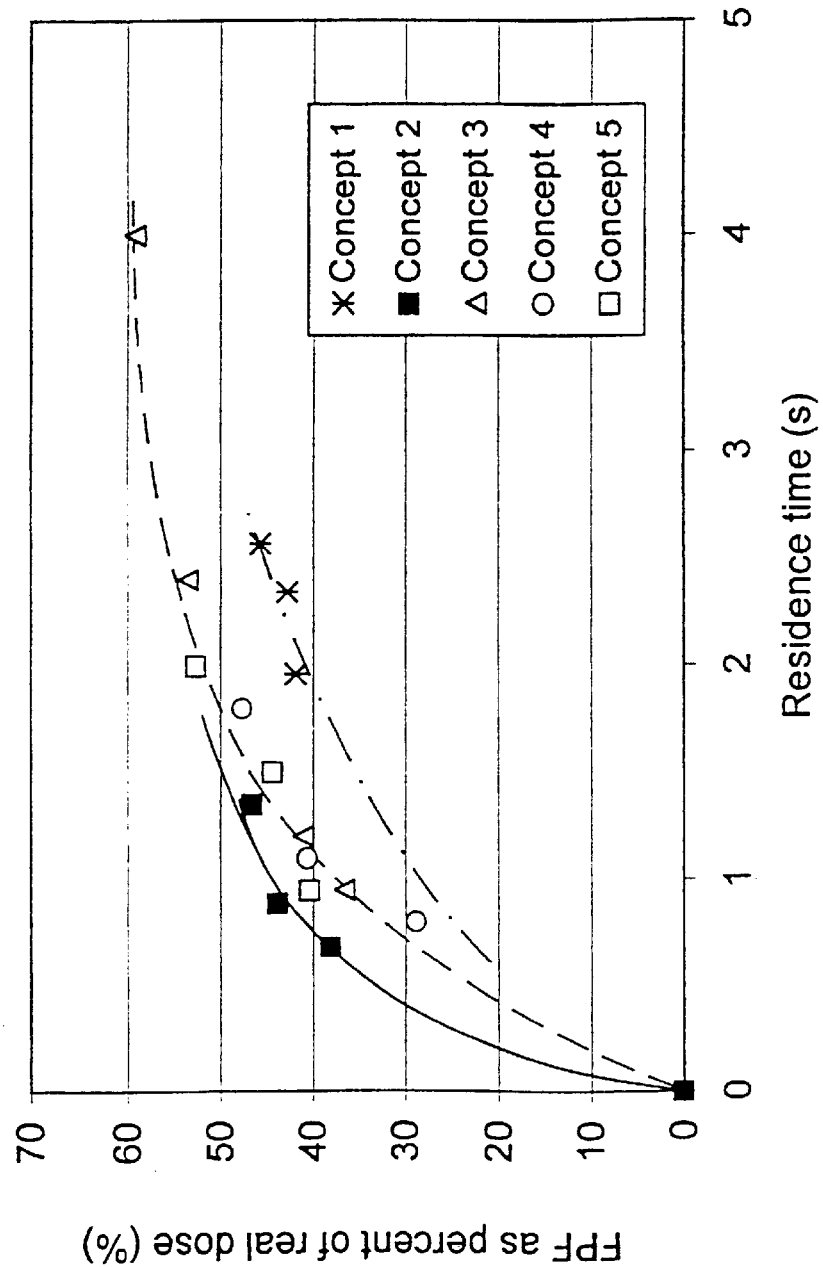
Figure 12A:
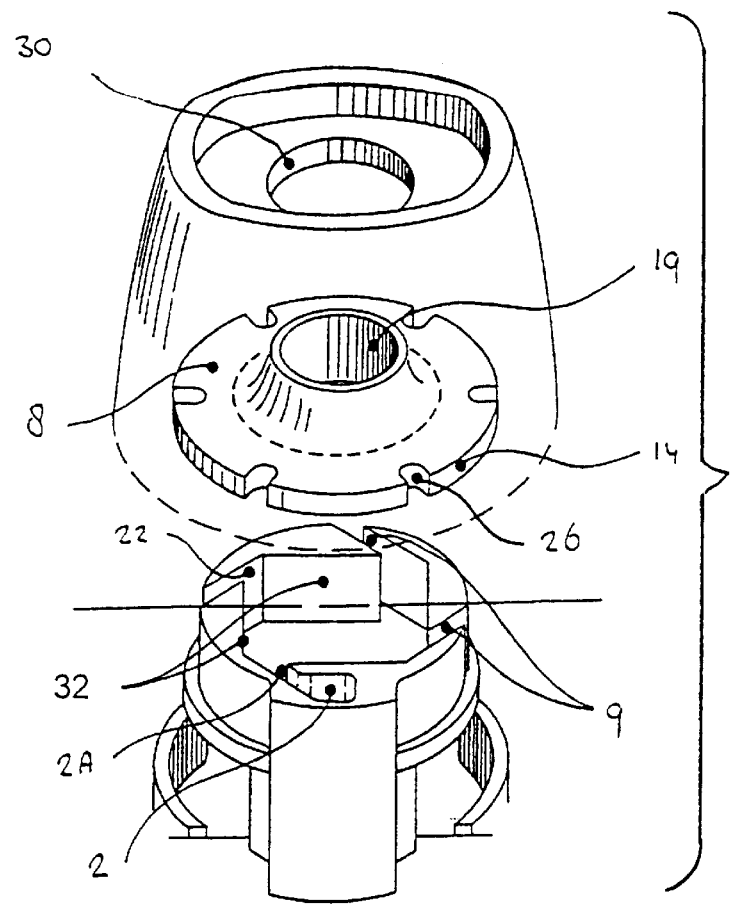
Figure 12B:
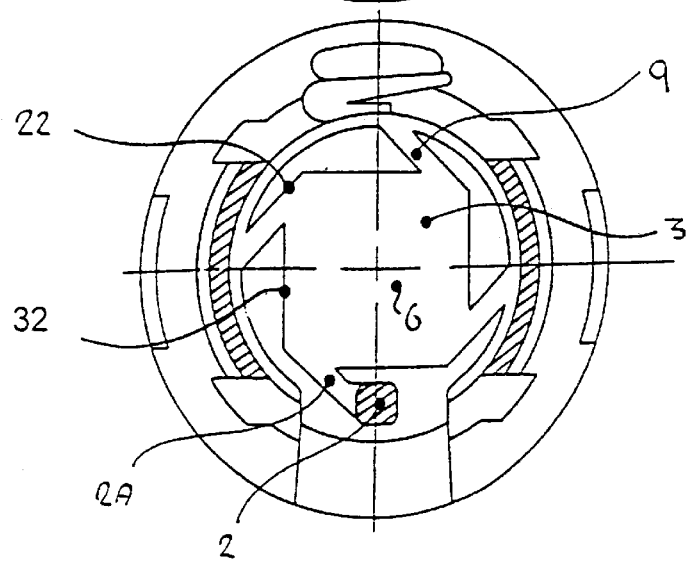

Another concept of the disintegration principle is depicted in FIG. 12. For this concept, the shape of the circulation chamber 3 is basically that of an octagon, but the eight sides of the octagon have two different lengths. Four longer sides 32 of preferably generally identical length alternate with four shorter sides 22 of preferably generally identical length. The longer sides 32 serve as the acceleration zones for the agglomerates which have relatively high inertia and require a certain distance over which they can be dragged by the air stream in order to increase velocity, whereas the shorter sides 22 serve as the impact zones for these particles. The number of channels 9 for the bypass flow has been reduced to three, compared to the concept depicted in FIG. 11. The cross section of these channels is generally rectangular, and the cross sectional area per channel 9 is slightly higher than that for the bypass channels 9 in the concept shown in FIG. 11. In spite of that, the sum of cross sectional areas for all channels 9 is lower than that of the concept in FIG. 11. As a result, the air velocity inside the channels 9 for the bypass flow is highest for the concept in FIG. 12, whereas the total air flow resistance of this passageway for the bypass flow is slightly higher, too.

As for the concept depicted in FIG. 11, the discharge channel 19 has no part 19A projecting into the circulation chamber 3. The inner diameter of the channel 19 is adapted to the desired residence time of carrier crystals inside the circulation chamber 3. By varying this diameter, the region inside the chamber 3, from which the carrier particles are able to enter the channel 19, can be controlled, as has been shown in FIG. 8, where similar symbols represent the residence times of the same concept however, with different diameters for the discharge channel 19. Top plates 8 connected to discharge channels 19 having different diameters, can be the same in every other respect, as shown in FIGS. 13B1–B3, except for the number of nicks 26 for the sheath flow (optionally, but not necessarily). They have matching mouthpiece cylinders 13 of which the circular holes 28 in their top plates 20 are adjusted to the exterior diameters of the channel 19 in such a way that the cross sectional areas for sheath flow through the annular channels 21 between the inner walls 30 of the circular holes 28 and the exterior walls 24 of the discharge channels 19 are approximately the same. The number of nicks 26 for the sheath flow along the circumference 14 of the top plate 8 for the circulation chamber 3 may be varied (FIG. 13B1) in order to fine tune the air flow resistance of the total passage way for sheath flow, relative to the air flow resistance of the circulation chamber 3.

In another embodiment of the top plate 8 for the circulation chamber 3, the discharge channel 19 has two different sections, one upper section 23A having a constant inner diameter and a lower section 23B having an increasing diameter towards the circulation chamber (FIG. 13B4). The transition is approximately at the midpoint of the channel 19. The lower part of this channel 19 has the shape of a frustum. For control of the carrier residence time inside the circulation chamber 3, the width of the base of this frustum may be varied. This has the advantage that no adaptation of the mouthpiece channel 13 is necessary and that different discharge channels 19, providing different residence times, can be used in combination with the same mouthpiece cylinder 13.

FIG. 13C shows a top plate 8 for the circulation chamber 3 with discharge channels 19 having longitudinal ridges 31 at equal distances from each other on their inner walls. Such longitudinal ridges 31, extending over the total length of the discharge channel 19 and projecting from its inner wall 23 into the channel 19 over a distance being less than the inner diameter of the channel 19, are able to transform particle movement inside this channel 19 substantially from helical into longitudinal direction. This reduces the deposition in the front of the mouth from centrifugal swing of particles with relatively large inertia, such as carrier crystals, which still bear part of the drug dose on their surface after leaving the circulation chamber 3. This reduces the mouth feel, but increases the throat deposition. For most applications, a design without these ridges 31 will therefore be preferable. The ridges 31 may project so far into the discharge channel 19, that they reach each other and comprise a solid framework 34 which in top view has the shape of a cross (FIG. 13D).

Finally, in FIG. 13(E) a design is shown bottom up in which the top plate 8 of the circulation chamber 3 is an integral part of this chamber. Such a construction has the advantage, that the transition of the longitudinal part of the powder channel 2 into the final section 2A, which is a tangent to the circulation chamber 3 and in which the flow direction is perpendicular to that in section 2, can be constructed with a certain rounding 33. Such a rounding provides a substantial reduction of the powder accumulation in this flow transition zone.

| Schedule of reference Numerals | |
|---|---|
| 1 | Body of inhaler |
| 2 | Powder channel |
| 2A | Final section of 2 |
| 3 | Circulation chamber |
| 4 | Rounding |
| 5 | Cylindrical wall of 3 |
| 6 | Bottom wall of 3 |
| 7 | Top plate of 1 |
| 8 | Top plate |
| 9 | Bypass flow channel |
| 10 | Cylindrical wall (Außenseite) of 3 |
| 10B | Thinner section of 10 |
| 11 | Opening |
| 12 | Annular chamber |
| 13 | Mouthpiece cylinder |
| 14 | Circumference of 8 |
| 14A | Diameters of 8 |
| 14B | Diameters of 8 |
| 15 | Projections |
| 15A | Gaps for 15 |
| 16 | Raised border |
| 17 | Rim of 10 |

-continued

| Schedule of reference Numerals | |
|---|---|
| 18 | Space |
| 19 | Discharge channel |
| 19A | Lower part of 19 |
| 19B | Other part of 19 |
| 19C | Top rim of 19 |
| 20 | Top plate |
| 21 | Annular passageway |
| 22 | Remaining sections of 5 |
| 23 | Inner wall of 19 |
| 23A | Upper section of 23 |
| 23B | Lower section of 23 |
| 24 | Outer wall of 19 |
| 25 | Cavity |
| 26 | Nicks |
| 27 | Top rim of 13 |
| 28 | Circular hole in 20 |
| 29 | Bottom rim of 13 |
| 30 | Inner walls of 28 |
| 31 | Longitudinal ridges |
| 32 | Longer sides (vgl. 22) |
| 33 | Rounding |
| 34 | Framework |
| 35 | Central Axis |

While this invention has been described as having an exemplary design, the present invention may be further modified within the spirit and scope of this disclosure. This application is therefore intended to cover any variations, uses, or adaptations of the invention using its general principles.

What is claimed is:

1. A dry powder inhaler comprising:

a circulation chamber wall, a top wall and a bottom wall together defining a circulation chamber having a central axis, a distance between said top and bottom walls defining a chamber height, said circulation chamber wall defining a circumference of said circulation chamber and a chamber diameter, said chamber height being less than said chamber diameter;

a first supply channel defining a first opening in said circulation chamber wall, said first supply channel in communication with a powder supply region and wherein said first supply channel conveys air and powder to said circulation chamber, said first supply channel oriented to direct conveyed air and powder into said circulation chamber in a direction substantially tangential to said circumference of said circulation chamber;

a plurality of second air supply channels each defining a second opening in said circulation chamber wall, said second openings and said first opening positioned substantially symmetrically about said central axis, each said second air supply channel in communication with a source of air wherein each said second air supply channel conveys substantially powder-free air to said circulation chamber, each said second air supply channel oriented to direct conveyed air into said circulation chamber in a direction substantially tangential to said circumference of said circulation chamber, said first supply channel and each of said second air supply channels oriented to convey air into said circulation chamber in a common rotational direction about said central axis whereby air and powder are conveyed within said circulation chamber in a generally circular flow pattern;

a discharge channel positioned substantially coaxially with said circulation chamber, said discharge channel having a first end and an opposite second end, said discharge channel having a portion extending through said top wall, said first end defining an inlet positioned within said circulation chamber and between said bottom wall and said top wall, said discharge channel portion disposed within said circulation chamber having an outer perimeter spaced radially inwardly from said circulation chamber wall, said second end defining a discharge opening; and a third air supply channel in communication with a source of air wherein said third air supply channel conveys substantially powder-free air, said third air supply channel defining an outlet positioned coaxially with said second end wherein said outlet forms an annular opening surrounding an exterior surface of said discharge channel at said second end and whereby said third air supply channel supplies a sheath of powder-free air surrounding powder-laden air discharged from said second end.

2. The dry powder inhaler of claim 1 wherein said plurality of second air supply channels consists of seven second air supply channels.

3. The dry powder inhaler of claim 1 wherein said top wall further comprises a flange extending radially outwardly of said circulation chamber wall, said flange defining passages therethrough, said passages forming a portion of said third air supply channel.

4. The dry powder inhaler of claim 1 wherein said first opening and each of said second openings have a substantially rectangular shape.

5. The dry powder inhaler of claim 1 wherein said first opening and said second openings have a top edge positioned adjacent said top wall and have a bottom edge positioned approximately midway between said top wall and said bottom wall.

6. The dry powder inhaler of claim 5 wherein said discharge channel extends into said circulation chamber by a distance greater than one half said chamber height whereby said inlet is positioned closer to said bottom wall than to said top wall.

7. A dry powder inhaler comprising:

a circulation chamber wall, a top wall and a bottom wall together defining a circulation chamber having a central axis, a distance between said top and bottom walls defining a chamber height, said circulation chamber wall defining a circumference of said circulation chamber and a chamber diameter, said chamber height being less than said chamber diameter;

a first supply channel defining a first opening in said circulation chamber wall, said first supply channel in communication with a powder supply region and wherein said first supply channel conveys air and powder to said circulation chamber, said first supply channel oriented to direct conveyed air and powder into said circulation chamber in a direction substantially tangential to said circumference of said circulation chamber;

at least one second air supply channel defining at least one second opening in said circulation chamber wall, said at least one second opening and said first opening positioned substantially symmetrically about said central axis, said at least one second air supply channel in communication with a source of air wherein said at least one second air supply channel conveys substantially powder-free air to said circulation chamber, said at least one second air supply channel oriented to direct conveyed air into said circulation chamber in a direction substantially tangential to said circumference of said circulation chamber, said first and second air supply channels oriented to convey air into said circulation chamber in a common rotational direction about said central axis whereby air and powder are conveyed within said circulation chamber in a generally circular flow pattern;

a discharge channel positioned substantially coaxially with said circulation chamber, said discharge channel having a first end and an opposite second end, said first end defining an inlet in communication with said circulation chamber, said second end defining a discharge opening for discharging powder-laden air; and wherein said circulation chamber wall is defined by a plurality of wall segments, each of said wall segments being substantially planar and having a height extending from said bottom wall to said top wall, said plurality of wall segments comprising a plurality of long wall segments and a plurality of short wall segments, each of said long wall segments having a length no less than a first length and each of said short wall segments having a length no greater than a second length, said first length being greater than said second length, said long wall segments and said short wall segments being alternatively positioned along said circumference of said circulation chamber wherein one of said short wall segments is positioned at an angle to and, with respect to said circular flow pattern, downstream of each of said long wall segments.

8. The dry powder inhaler of claim 7 wherein each of said long wall segments is positioned at an approximately 135 degree angle to said short wall segment positioned downstream thereof.

9. The dry powder inhaler of claim 7 further comprising a third air supply channel in communication with a source of air wherein said third air supply channel conveys substantially powder-free air, said third air supply channel defining an outlet positioned coaxially with said second end wherein said outlet forms an annular opening surrounding an exterior surface of said discharge channel at said second end and whereby said third air supply channel supplies a sheath of powder-free air surrounding powder-laden air discharged from said second end.

10. The dry powder inhaler of claim 7 wherein said at least one second opening comprises 3 to 8 second openings positioned substantially symmetrically about said central axis and oriented to direct powder-free air into said circulation chamber in a direction substantially tangential to an interior surface of said circulation chamber wall and in said common rotational direction and wherein said plurality of long wall segments is equal in number to a total number of said second openings and said first opening, and said plurality of short wall segments is equal in number to said total number of said second openings and said first opening.

11. The dry powder inhaler of claim 10 wherein said at least one second opening consists of 3 second openings.

12. A dry powder inhaler comprising:

a circulation chamber wall, a top wall and a bottom wall together defining a circulation chamber having a central axis, a distance between said top and bottom walls defining a chamber height, said circulation chamber wall defining a circumference of said circulation chamber and a chamber diameter, said chamber height being less than said chamber diameter;

a first supply channel defining a first opening in said circulation chamber wall, said first supply channel in communication with a powder supply region and wherein said first supply channel conveys air and powder to said circulation chamber, said first supply channel oriented to direct conveyed air and powder into said circulation chamber in a direction substantially tangential to said circumference of said circulation chamber;

a plurality of second air supply channels defining a plurality of second openings in said circulation chamber wall, said second openings and said first opening positioned substantially symmetrically about said central axis, said second air supply channels in communication with a source of air wherein said second air supply channels convey substantially powder-free air to said circulation chamber, each of said second air supply channels oriented to direct conveyed air into said circulation chamber in a direction substantially tangential to said circumference of said circulation chamber, said first supply channel and each of said second air supply channels oriented to convey air into said circulation chamber in a common rotational direction about said central axis whereby air and powder are conveyed within said circulation chamber in a generally circular flow pattern;

a discharge channel positioned substantially coaxially with said circulation chamber, said discharge channel having a first end and an opposite second end, said first end defining an inlet in communication with said circulation chamber, said second end defining a discharge opening for discharging powder-laden air; and wherein said circulation chamber wall is defined by a plurality of wall segments, each of said wall segments being substantially planar and having a height extending from said bottom wall to said top wall, each of said wall segments positioned in pairs wherein each said pair comprises two intersecting wall segments forming an angle of approximately 135 degrees and said first opening and said second openings are positioned to separate each said pair of wall segments from an adjacent one of said pairs of wall segments.

13. The dry powder inhaler of claim 12 further comprising a third air supply channel in communication with a source of air wherein said third air supply channel conveys substantially powder-free air, said third air supply channel defining an outlet positioned coaxially with said second end wherein said outlet forms an annular opening surrounding an exterior surface of said discharge channel at said second end and whereby said third air supply channel supplies a sheath of powder-free air surrounding powder-laden air discharged from said second end.

14. The dry powder inhaler of claim 12 wherein said plurality of second openings comprises 3 to 8 second openings.

15. The dry powder inhaler of claim 14 wherein said plurality of second openings consists of 3 second openings.

16. A dry powder inhaler comprising:

a circulation chamber wall, a top wall and a bottom wall together defining a circulation chamber having a central axis, a distance between said top and bottom walls defining a chamber height, said circulation chamber wall defining a circumference of said circulation chamber and a chamber diameter, said chamber height being less than said chamber diameter;

a first supply channel defining a first opening in said circulation chamber wall, said first supply channel in communication with a powder supply region and wherein said first supply channel conveys air and powder to said circulation chamber, said first supply channel oriented to direct conveyed air and powder into said circulation chamber in a direction substantially tangential to said circumference of said circulation chamber;

at least one second air supply channel defining a second opening in said circulation chamber wall, said second opening and said first opening positioned substantially symmetrically about said central axis, said second air supply channel in communication with a source of air wherein said second air supply channel conveys substantially powder-free air to said circulation chamber, said second air supply channel oriented to direct conveyed air into said circulation chamber in a direction substantially tangential to said circumference of said circulation chamber, said first supply channel and said second air supply channel oriented to convey air into said circulation chamber in a common rotational direction about said central axis whereby air and powder are conveyed within said circulation chamber in a substantially circular flow pattern;

a discharge channel positioned substantially coaxially with said circulation chamber, said discharge channel having a first end and an opposite second end, said discharge channel extending through said top wall, said first end defining an inlet positioned within said circulation chamber and between said bottom wall and said top wall, said discharge channel disposed within said circulation chamber having an outer perimeter spaced radially inwardly from said chamber wall, said second end defining a discharge opening; and a third air supply channel in communication with a source of air wherein said third air supply channel conveys substantially powder-free air, said third air supply channel defining an outlet positioned coaxially with said second end wherein said outlet forms an annular opening surrounding an exterior surface of said discharge channel at said second end and whereby said third air supply channel supplies a sheath of powder-free air surrounding powder-laden air discharged from said second end; and wherein said top wall defines a flange extending radially outwardly of said circulation chamber wall, said flange defining passages therethrough, said passages forming a portion of said third air supply channel.

17. A dry powder inhaler comprising:

a circulation chamber wall, a top wall and a bottom wall together defining a circulation chamber having a central axis, a distance between said top and bottom walls defining a chamber height, said circulation chamber wall defining a circumference of said circulation chamber and a chamber diameter, said chamber height being less than said chamber diameter;

a first supply channel defining a first opening in said circulation chamber wall, said first supply channel in communication with a powder supply region and wherein said first supply channel conveys air and powder to said circulation chamber, said first supply channel oriented to direct conveyed air and powder into said circulation chamber in a direction substantially tangential to said circumference of said circulation chamber;

at least one second air supply channel defining at least one second opening in said circulation chamber wall, said at least one second opening and said first opening positioned substantially symmetrically about said central axis, said at least one second air supply channel in communication with a source of air wherein said at least one second air supply channel conveys substantially powder-free air to said circulation chamber, said at least one second air supply channel oriented to direct conveyed air into said circulation chamber in a direction substantially tangential to said circumference of said circulation chamber, said first supply channel and said second air supply channel oriented to convey air into said circulation chamber in a common rotational direction about said central axis whereby air and powder are conveyed within said circulation chamber in a substantially circular flow pattern;

a discharge channel positioned substantially coaxially with said circulation chamber, said discharge channel extending from a first end to an opposite second end and having an interior surface defining a substantially circular cross sectional shape, said discharge channel having a portion extending through said top wall, said first end defining an inlet positioned within said circulation chamber and between said bottom wall and said top wall, said portion of said discharge channel disposed within said circulation chamber having an outer perimeter spaced radially inwardly from said chamber wall, said second end defining a discharge opening; and a baffle member positioned in said discharge channel to disrupt helical flow of particles through said discharge channel and direct particles in a direction substantially parallel to said central axis.

18. The dry powder inhaler of claim 17 wherein said baffle member comprises a plurality of ridges projecting radially inwardly from said interior surface and extending parallel to said central axis, said interior surface defining a discharge diameter and said ridges projecting inwardly a distance less than said discharge diameter.

19. The dry powder inhaler of claim 17 wherein said baffle member comprises a plurality of baffle frameworks extending between diametrically opposite sides of said interior surface and each of said frameworks being positioned at spaced locations along said central axis.

20. The dry powder inhaler of claim 19 wherein said frameworks are cross-shaped.

21. The dry powder inhaler of claim 17 further comprising a third air supply channel in communication with a source of air wherein said third air supply channel conveys substantially powder-free air, said third air supply channel defining an outlet positioned coaxially with said second end wherein said outlet forms an annular opening surrounding an exterior surface of said discharge channel at said second end and whereby said third air supply channel supplies a sheath of powder-free air surrounding powder-laden air discharged from said second end.

22. A modular dry powder inhaler system comprising:

an inhaler body having a circulation chamber wall and a bottom wall defining a portion of a circulation chamber having a central axis, said circulation chamber wall defining a circumference of said circulation chamber;

a first supply channel defining a first opening in said circulation chamber wall, said first supply channel in communication with a powder supply region and wherein said first supply channel conveys air and powder to said circulation chamber; said first supply channel oriented to direct conveyed air and powder into said circulation chamber in a direction substantially tangential to said circumference of said circulation chamber;

at least one second air supply channel defining at least one second opening in said circulation chamber wall, said at least one second opening and said first opening positioned substantially symmetrically about said central axis, said at least one second air supply channel in communication with a source of air wherein said at least one second air supply channel conveys substantially powder-free air to said circulation chamber, said at least one second air supply channel oriented to direct conveyed air into said circulation chamber in a direction substantially tangential to said circumference of said circulation chamber, said first and second air supply channels oriented to convey air into said circulation chamber in a common rotational direction about said central axis whereby air and powder are conveyed within said circulation chamber in a substantially circular flow pattern;

a plurality of top plates, each of said top plates being removably mountable to said inhaler body and, when mounted to said inhaler body, forming a top wall of said circulation chamber wherein a distance between said top and bottom walls defines a chamber height and said circulation chamber wall defines a chamber diameter, said chamber height being less than said chamber diameter, each said top plate further defining a discharge channel positionable substantially coaxially with said circulation chamber, each said discharge channel having a first end and an opposite second end, said first ends defining an inlet opening in communication with said circulation chamber and said second ends defining a discharge opening for discharging powder-laden air when mounted to said inhaler body, said plurality of top plates having a plurality of different configurations whereby a selected one of said top plates can be attached to said inhaler housing based upon user requirements.

23. The modular dry powder inhaler system of claim 22 further comprising a mouthpiece removably mountable to said inhaler body, attachment of said mouthpiece to said inhaler body securing said selected one of said top plates to said inhaler body, said mouthpiece defining a third air supply channel in communication with a source of air wherein said third air supply channel conveys substantially powder-free air, said third air supply channel defining an outlet positioned coaxially with said second end of said selected top plate wherein said outlet forms an annular opening surrounding an exterior surface of said discharge channel at said second end of said selected top plate and whereby said third air supply channel supplies a sheath of powder-free air surrounding the powder-laden air discharged from said second end of said selected top plate.

24. The modular dry powder inhaler system of claim 23 wherein each of said plurality of top plates defines a flange extending radially outwardly of said circulation chamber wall, said flanges defining passages therethrough, said passages of said selected top plate forming a portion of said third air supply channel.

25. The modular dry powder inhaler system of claim 23 wherein said plurality of top plates each define a discharge channel wherein each of said second ends have a common discharge opening diameter and wherein said first ends define a plurality of different inlet opening diameters.

26. The modular dry powder inhaler system of claim 22 wherein at least one of said top plates has a discharge channel defining a substantially circular cross sectional shape and further comprises a baffle member positioned in said discharge channel to disrupt helical flow of particles through said discharge channel and direct particles in a direction substantially parallel to said central axis when mounted to said inhaler body.

* * * * *